US012205718B2

(12) United States Patent
Derdzinski et al.

(10) Patent No.: US 12,205,718 B2
(45) Date of Patent: Jan. 21, 2025

(54) GLUCOSE PREDICTION USING MACHINE LEARNING AND TIME SERIES GLUCOSE MEASUREMENTS

(71) Applicant: DexCom, Inc., San Diego, CA (US)

(72) Inventors: Mark Derdzinski, La Jolla, CA (US); Andrew Scott Parker, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 50 days.

(21) Appl. No.: 17/112,870

(22) Filed: Dec. 4, 2020

(65) Prior Publication Data

US 2021/0369151 A1 Dec. 2, 2021

Related U.S. Application Data

(60) Provisional application No. 63/030,492, filed on May 27, 2020.

(51) Int. Cl.
*G16H 40/67* (2018.01)
*A61B 5/00* (2006.01)
(Continued)

(52) U.S. Cl.
CPC ........... *G16H 40/67* (2018.01); *A61B 5/0004* (2013.01); *A61B 5/0015* (2013.01);
(Continued)

(58) Field of Classification Search
CPC ... A61B 5/0004; A61B 5/0015; A61B 5/6801; A61B 5/7275; A61B 5/746;
(Continued)

(56) References Cited

U.S. PATENT DOCUMENTS 6,280,381 B1 8/2001 Malin et al.
7,727,147 B1 6/2010 Osorio et al.
(Continued)

FOREIGN PATENT DOCUMENTS

CN 106714874 B 10/2019
CN 109480835 B 4/2021
(Continued)

OTHER PUBLICATIONS

Cappon G., et al., "A Bayesian Framework to Identify Type 1 Diabetes Physiological Models Using Easily Accessible Patient Data," 2019 41st Annual International Conference of the IEEE Engineering in Medicine and Biology Society (EMBC), Jul. 23, 2019, Retrieved on Jan. 10, 2022 from URL: https://ieeexplore.ieee.org/abstract/document/8856846, 4 pages.

(Continued)

*Primary Examiner* — David J. McCrosky
*Assistant Examiner* — Meghan R Kumar
(74) *Attorney, Agent, or Firm* — PATTERSON + SHERIDAN, LLP

(57) ABSTRACT

Glucose prediction using machine learning (ML) and time series glucose measurements is described. Given the number of people that wear glucose monitoring devices and because some wearable glucose monitoring devices can produce measurements continuously, a platform providing such devices may have an enormous amount of data. This amount of data is practically, if not actually, impossible for humans to process and covers a robust number of state spaces unlikely to be covered without the enormous amount of data. In implementations, a glucose monitoring platform includes an ML model trained using historical time series glucose measurements of a user population. The ML model predicts upcoming glucose measurements for a particular user by receiving a time series of glucose measurements up to a time (Continued)

and determining the upcoming glucose measurements of the particular user for an interval subsequent to the time based on patterns learned from the historical time series glucose measurements.

20 Claims, 14 Drawing Sheets

(51) Int. Cl.
*A61B 5/145* (2006.01)
*G06F 17/18* (2006.01)
*G06N 3/044* (2023.01)
*G06N 3/08* (2023.01)
*G16H 40/63* (2018.01)
*G16H 50/20* (2018.01)
*G06N 3/02* (2006.01)
*G06N 3/0442* (2023.01)
*H04L 67/12* (2022.01)

(52) U.S. Cl.
CPC ........ *A61B 5/14532* (2013.01); *A61B 5/6801* (2013.01); *A61B 5/7275* (2013.01); *A61B 5/746* (2013.01); *G06F 17/18* (2013.01); *G06N 3/044* (2023.01); *G06N 3/08* (2013.01); *G16H 40/63* (2018.01); *G16H 50/20* (2018.01); *A61B 5/74* (2013.01); *G06N 3/02* (2013.01); *G06N 3/0442* (2023.01); *H04L 67/12* (2013.01)

(58) Field of Classification Search
CPC . A61B 5/14532; A61B 5/0022; A61B 5/6833; A61B 5/7267; G16H 40/67; G16H 40/63; G16H 50/20; G16H 50/70; G06F 17/18; G06N 3/044; G06N 3/048
See application file for complete search history.

(56) References Cited

U.S. PATENT DOCUMENTS

| 11,298,071 | B1 | 4/2022 | Saghafi et al. | |
|---|---|---|---|---|
| 2010/0262117 | A1 | 10/2010 | Magni et al. | |
| 2011/0098548 | A1 | 4/2011 | Budiman et al. | |
| 2011/0184267 | A1 | 7/2011 | Duke et al. | |
| 2013/0109944 | A1 | 5/2013 | Sparacino et al. | |
| 2014/0088393 | A1 | 3/2014 | Bernstein et al. | |
| 2014/0118166 | A1* | 5/2014 | Hampapuram | A61B 5/4866 340/870.16 |
| 2014/0309615 | A1 | 10/2014 | Mazlish | |
| 2016/0198988 | A1* | 7/2016 | Bhavaraju | A61B 5/1495 600/365 |
| 2016/0342754 | A1 | 11/2016 | Vettoretti et al. | |
| 2016/0354543 | A1 | 12/2016 | Cinar et al. | |
| 2017/0074757 | A1 | 3/2017 | Garcia et al. | |
| 2017/0224291 | A1* | 8/2017 | Hampapuram | A61B 5/14532 |
| 2017/0252513 | A1 | 9/2017 | Buck, Jr. et al. | |
| 2018/0116573 | A1 | 5/2018 | Steiger et al. | |
| 2018/0174675 | A1 | 6/2018 | Roy et al. | |
| 2018/0184952 | A1 | 7/2018 | Roy et al. | |
| 2018/0192927 | A1* | 7/2018 | Taub | G16H 40/67 |
| 2018/0272063 | A1 | 9/2018 | Neemuchwala et al. | |
| 2019/0114531 | A1 | 4/2019 | Torkamani et al. | |
| 2019/0328966 | A1 | 10/2019 | Chase et al. | |
| 2019/0336684 | A1 | 11/2019 | O'Connor et al. | |
| 2020/0237271 | A1 | 7/2020 | Vanslyke et al. | |
| 2020/0375549 | A1 | 12/2020 | Wexler et al. | |
| 2021/0038163 | A1 | 2/2021 | Agrawal et al. | |
| 2021/0050089 | A1 | 2/2021 | Mohammed et al. | |
| 2021/0285819 | A1 | 9/2021 | Poli et al. | |
| 2021/0369151 | A1 | 12/2021 | Derdzinski et al. | |
| 2021/0375447 | A1 | 12/2021 | Derdzinski et al. | |
| 2021/0390399 | A1 | 12/2021 | Georgiou et al. | |
| 2022/0061676 | A1 | 3/2022 | Wilson et al. | |

FOREIGN PATENT DOCUMENTS

| EP | 3438986 A1 | 2/2019 |
|---|---|---|
| WO | 2006075133 A1 | 7/2006 |
| WO | 2020089656 A1 | 5/2020 |
| WO | 2020187987 A1 | 9/2020 |

OTHER PUBLICATIONS

Contreras I., et al., "Personalized Blood Glucose Prediction: a Hybrid Approach Using Grammatical Evolution and Physiological Models," PloS one, Nov. 7, 2017, Retrieved on Jan. 10, 2022 from URL: https://journals.plos.org/plosone/article/comments?id=10.1371/journal.pone.0187754, 16 pages.
Eren-Oruklu M., et al., "Adaptive System Identification for Estimating Future Glucose Concentrations and Hypoglycemia Alarms," Automatica, vol. 48(8):1892-1897, Jun. 22, 2012, Retrieved on Jan. 10, 2022 from URL: www.ncbi.nlm.nih.gov/pmc/articles/PMC3409594/, 15 pages.
International Search Report and Written Opinion for Application No.PCT/US2021/059235, mailed Feb. 7, 2022, 17 pages.
International Search Report and Written Opinion dated Feb. 25, 2021 for Application No. PCT/US2020/063437, filed Dec. 4, 2020; 10 pages.
Astrom K.J., "Maximum Likelihood and Prediction Error Methods," Automatica, vol. 16(5), 1980, pp. 551-574.
Man C. D. et al.,"A System Model of Oral Glucose Absorption: Validation on Gold Standard Data," IEEE Trans. Biomed. Eng., vol. 53, No. 12, pp. 2472-2478, Dec. 2006.
Schiavon M., et al., "Modeling Subcutaneous Absorption of Fast-Acting Insulin in Type 1 Diabetes," IEEE Transactions on Biomedical Engineering, vol. 65(9), Sep. 9, 2018, pp. 2079-2086.
Visentin R., et al., "The UVA/Padova Type 1 Diabetes Simulator Goes From Single Meal to Single Day," Journal of Diabetes Science and Technology, vol. 12(2), 2018, pp. 273-281.

* cited by examiner

GLUCOSE PREDICTION USING MACHINE LEARNING AND TIME SERIES GLUCOSE MEASUREMENTS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Patent Application No. 63/030,492, filed May 27, 2020, and titled "Glucose Prediction Using Machine Learning and Time Series Glucose Measurements". The aforementioned application is incorporated by reference herein in its entirety, and is hereby expressly made a part of this specification.

BACKGROUND

Diabetes is a metabolic condition affecting hundreds of millions of people, and is one of the leading causes of death worldwide. For people living with diabetes, access to treatment is critical to their survival. With proper treatment, serious damage to the heart, blood vessels, eyes, kidneys, and nerves, due to diabetes can be largely avoided. Proper treatment for a person with Type I diabetes generally involves monitoring glucose levels throughout the day and regulating those levels—with some combination of insulin, eating, and exercise—so that the levels stay within a desired range. With advances in medical technologies a variety of systems for monitoring glucose levels have been developed.

While monitoring a person's current glucose level is useful for deciding how to treat diabetes, knowing what the person's glucose levels will be in the future is more useful. This is because it allows the person or a caregiver to take actions to mitigate potentially adverse health conditions, tied to changing glucose levels, before such health conditions occur. However, conventional techniques for predicting upcoming glucose levels may suffer from inaccuracies in various cases due to the manner in which they correlate observed glucose levels to future glucose levels. Conventional techniques also may fail to predict glucose levels at a correct time in the future.

By way of example, a system employing conventional glucose prediction techniques may output a prediction that is intended to indicate a person's glucose measurement 30 minutes into the future from a current time. However, the person's observed glucose may correspond to the predicted measurement a mere five minutes into the future. To this end, the prediction is 25 minutes delayed—the predictive horizon of the system fails to match the person's actual glucose. Failure of the predictive horizon to match actual glucose and inaccurate predictions may render glucose predictions generated by conventional systems unsuitable for various applications, such as for prescribing actions to mitigate dangerously (and rapidly) changing glucose levels.

SUMMARY

To overcome these problems, glucose prediction using machine learning and time series glucose measurements is leveraged. Given the number of people that wear glucose monitoring devices, such as continuous glucose monitoring (CGM) systems, and because those wearable devices can produce measurements continuously, a glucose monitoring platform that provides a glucose monitoring device with a sensor for detecting glucose levels, and maintains measurements produced by such a system may have an enormous amount of data, e.g., tens of millions of patient days' worth of measurements. However, this amount of data is practically, if not actually, impossible for a human to process to reliably identify patterns of a robust number of state spaces.

In one or more implementations, a glucose monitoring platform includes a machine learning model (e.g., a non-linear machine learning model) trained using historical time series glucose measurements of a user population, where the glucose measurements are provided by wearable glucose monitoring devices worn by users of the user population. Once trained, the machine learning model predicts upcoming glucose measurements for users. When predicting upcoming glucose measurements for a user, a time series of glucose measurements up to a time is received. The glucose measurements of this time series are provided by a wearable glucose monitoring device worn by the user. The machine learning model predicts upcoming glucose measurements of the user for an interval of time subsequent to the time. In particular, the machine learning model generates this prediction based on the training with the historical time series glucose measurements of the user population. The upcoming glucose measurements are then output, such as via communication and/or display of a notification about the upcoming glucose measurements.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Figure 1:
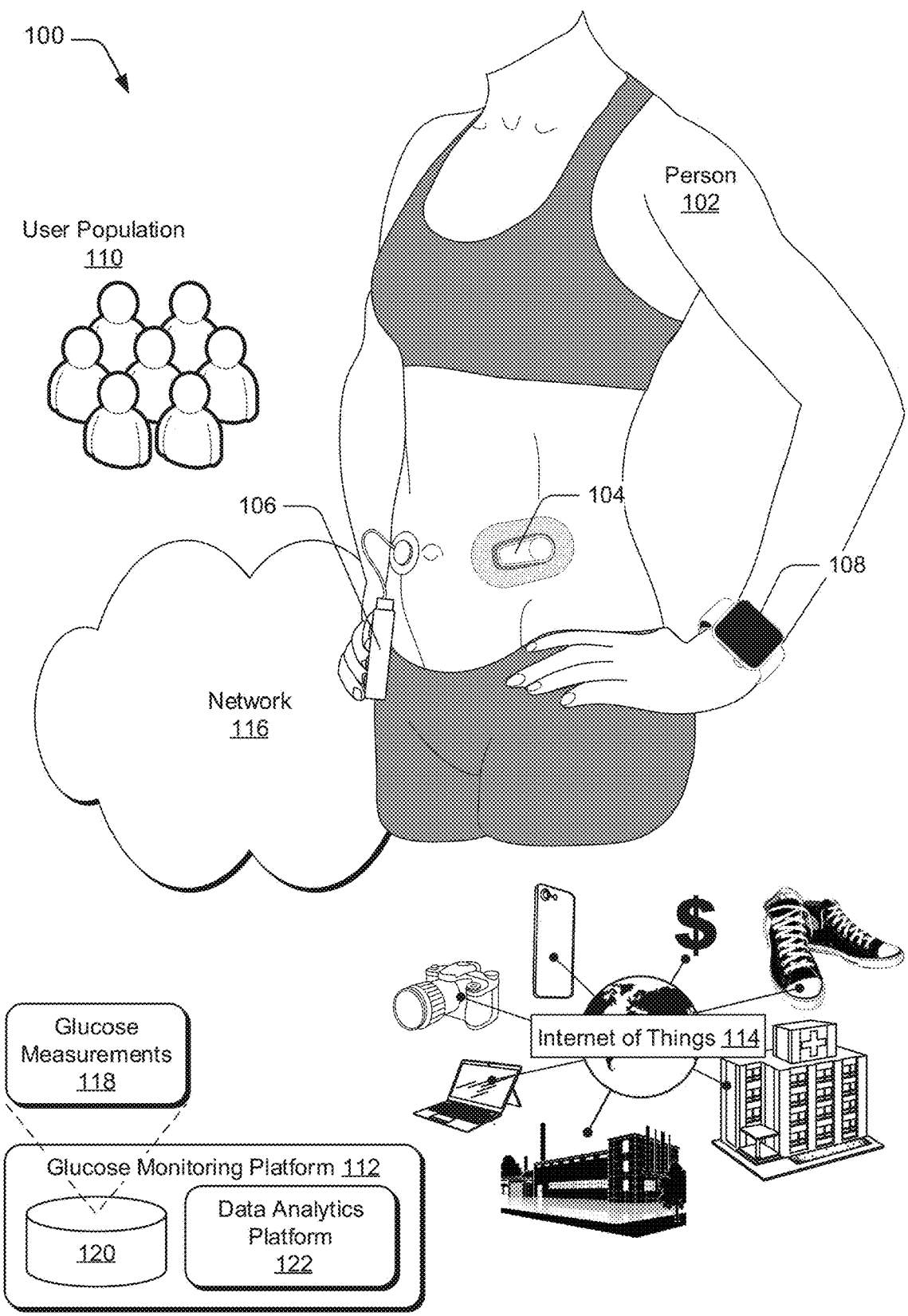
FIG. 1 is an illustration of an environment in an example implementation that is operable to employ techniques described herein.

Monitoring a person's glucose levels is useful for deciding how to treat diabetes. Knowing what the person's glucose levels will be in the future is more useful though. This is because it allows the person or a caregiver to take action to mitigate potentially adverse health conditions tied to changing glucose levels (e.g., hyper- or hypo-glycemia) before such health conditions occur.

Conventional approaches to glucose prediction may model glucose using linear models, such as using autoregressive linear models. Although such linear models may be capable of describing time-varying processes, the output of those models is linearly dependent on previous values. This can result in glucose predictions that have significant time delays in relation to actual, observed glucose measurements. In other words, the predictive horizons of these models may fail to match a person's actual glucose. Additionally, linear models may generate inaccurate predictions of upcoming glucose measurements because the linear dependencies of those models may not allow them to robustly cover state spaces underlying tens of millions of patient days' worth of glucose measurements. Simply, linear models may not be able to account for some of the patterns observed in such historical data. Failure of predictive horizons to match actual glucose and inaccurate predictions (or predictions of limited accuracy) may render glucose predictions generated by conventional systems unsuitable for various applications, such as for prescribing actions to mitigate dangerously (and rapidly) changing glucose levels.

To overcome these problems, glucose prediction using machine learning and time series glucose measurements is leveraged. In one or more implementations, a glucose monitoring platform includes a machine learning model trained, using historical time series glucose measurements of a user population, to predict upcoming glucose measurements for an individual user. The glucose measurements of the user population and the individual user may be provided by wearable glucose monitoring devices worn by users of the user population and the individual user. By obtaining measurements produced by these wearable glucose monitoring devices and maintaining the measurements, the glucose monitoring platform may have an enormous amount of data, e.g., tens of millions of patient days' worth of measurements. Conventional linear models may not be able to model some of the patterns observed in this wealth of historical data.

In contrast to conventional approaches, the machine learning model described herein may be configured as a non-linear model, or as an ensemble of models that includes one or more non-linear models. Such non-linear machine learning models may include, for instance, neural networks (e.g., recurrent neural networks such as long-short term memory (LSTM) networks), state machines, Markov chains, Monte Carlo methods, and particle filters, to name just a few. Such models may be capable of capturing patterns of state spaces that linear techniques simply cannot model.

Once the machine learning model is trained, it is used to predict upcoming glucose measurements for users. When predicting upcoming glucose measurements for a particular user, a time series of glucose measurements up to a time is received, e.g., a last 12 hours of glucose measurements. The glucose measurements of this time series are provided by the wearable glucose monitoring device worn by the user. Responsive to receiving the time series as input, the machine learning model predicts upcoming glucose measurements for an interval of time subsequent to the time, e.g., a next 30 minutes. The machine learning model generates this prediction based on its training with the historical time series glucose measurements of the user population. The upcoming glucose measurements are then output, such as for generating a notification about the upcoming glucose measurements. This notification may be communicated over a network to one or more computing devices, including a computing device associated with the user (e.g., for output via an application of the glucose monitoring platform), a computing device associated with a health care provider, or a computing device associated with a telemedicine service, to name just a few.

By predicting upcoming glucose measurements and notifying users, health care providers, and/or telemedicine services about the upcoming glucose measurements, the described machine learning model allows actions to be taken to mitigate potentially adverse health conditions before those health conditions occur. Advantageously, the more accurate and timely predictions of upcoming glucose provided by the described machine learning model allow users and various other parties to make better informed decisions regarding how to treat diabetes and achieve better outcomes in through the treatment. In so doing, serious damage to the heart, blood vessels, eyes, kidneys, and nerves, and death due to diabetes can be largely avoided.

In addition, for a person with diabetes, treatment decisions may be influenced by the person's impending or predicted upcoming glucose measurements. For instance, decision support services of a glucose monitoring platform (e.g., via an application, notifications, and so on) may use impending or predicted upcoming glucose measurements to inform and assist users in their treatment. By way of example, such informing and assisting can be responsive to detection of impending or possible events that are predicted to occur when patients are unable to self-monitor their glucose, e.g., when they are sleeping. While notifications such as short-term predictive alarms and threshold alerts may be able to address the need to alert patients about impending events, conventional prediction techniques are not capable of accurately predicting glucose measurements for a time horizon that is further in the future from a current time, e.g., on the scale of hours or more. Accordingly, conventional techniques are unsuitable for accurately predicting whether a patient will experience overnight hypoglycemia. The machine learning models described above and below more accurately predict glucose of a person for time horizons further into the future than conventional techniques. Accordingly, the described machine learning models can be leveraged in connection with prediction of longer-term glycemic outcomes, such as whether a patient will experience overnight hypoglycemia.

In the following discussion, an example environment is first described that may employ the techniques described herein. Example implementation details and procedures are then described which may be performed in the example environment as well as other environments. Performance of the example procedures is not limited to the example environment and the example environment is not limited to performance of the example procedures.

Example Environment

FIG. 1 is an illustration of an environment 100 in an example implementation that is operable to employ glucose prediction using machine learning and time series glucose measurements as described herein. The illustrated environment 100 includes person 102, who is depicted wearing a wearable glucose monitoring device 104, insulin delivery system 106, and computing device 108. The illustrated environment 100 also includes other users in a user population 110 that wear wearable glucose monitoring devices, glucose monitoring platform 112, and Internet of Things 114 (IoT 114). The wearable glucose monitoring device 104, insulin delivery system 106, computing device 108, user population 110, glucose monitoring platform 112, and IoT 114 are communicatively coupled, including via a network 116.

Alternately or additionally, one or more of the wearable glucose monitoring device 104, the insulin delivery system 106, and the computing device 108 may be communicatively coupled in other ways, such as using one or more wireless communication protocols or techniques. By way of example, the wearable glucose monitoring device 104, the insulin delivery system 106, and the computing device 108 may communicate with one another using one or more of Bluetooth (e.g., Bluetooth Low Energy links), near-field communication (NFC), 5G, and so forth. The wearable glucose monitoring device 104, the insulin delivery system 106, and the computing device 108 may leverage these types of communication to form a closed-loop system between one another. In this way, the insulin delivery system 106 may deliver insulin based on sequences of glucose measurements in real-time as glucose measurements are obtained by the wearable glucose monitoring device 104 and as future glucose measurements are predicted.

In accordance with the described techniques, the wearable glucose monitoring device 104 is configured to monitor glucose of the person 102, e.g., continuously. In one or more implementations, the wearable glucose monitoring device 104 is a continuous glucose monitoring (CGM) system. As used herein, the term "continuous" when used in connection with glucose monitoring may refer to an ability of a device to produce measurements substantially continuously, such that the device may be configured to produce the glucose measurements 118 at intervals of time (e.g., every hour, every 30 minutes, every 5 minutes, and so forth), responsive to establishing a communicative coupling with a different device (e.g., when a computing device establishes a wireless connection with the wearable glucose monitoring device 104 to retrieve one or more of the measurements), and so forth. The wearable glucose monitoring device 104 may be configured with a glucose sensor, for instance, that continuously detects analytes indicative of the person 102's glucose and enables generation of glucose measurements. In the illustrated environment 100 these measurements are represented as glucose measurements 118. This functionality along with further aspects of the wearable glucose monitoring device 104's configuration are discussed in more detail in relation to FIG. 2.

In one or more implementations, the wearable glucose monitoring device 104 transmits the glucose measurements 118 to the computing device 108, such as via a wireless connection. The wearable glucose monitoring device 104 may communicate these measurements in real-time, e.g., as they are produced using a glucose sensor. Alternately or in addition, the wearable glucose monitoring device 104 may communicate the glucose measurements 118 to the computing device 108 at set time intervals, e.g., every 30 seconds, every minute, every 5 minutes, every hour, every 6 hours, every day, and so forth. Further still, the wearable glucose monitoring device 104 may communicate these measurements responsive to a request from the computing device 108, e.g., communicated to the wearable glucose monitoring device 104 when the computing device 108 predicts the person 102's upcoming glucose level, causes display of a user interface having information about the person 102's glucose level, updates such a display, and so forth. Accordingly, the computing device 108 may maintain the glucose measurements 118 of the person 102 at least temporarily, e.g., in computer-readable storage media of the computing device 108.

Although illustrated as a wearable device (e.g., a smart watch), the computing device 108 may be configured in a variety of ways without departing from the spirit or scope of the described techniques. By way of example and not limitation, the computing device 108 may be configured as a different type of mobile device (e.g., a mobile phone or tablet device). In one or more implementations, the computing device 108 may be configured as a dedicated device associated with the glucose monitoring platform 112, e.g., with functionality to obtain the glucose measurements 118 from the wearable glucose monitoring device 104, perform various computations in relation to the glucose measurements 118, display information related to the glucose measurements 118 and the glucose monitoring platform 112, communicate the glucose measurements 118 to the glucose monitoring platform 112, and so forth. In contrast to implementations where the computing device 108 is configured as a mobile phone, however, the computing device 108 may not include some functionality available with mobile phone or wearable configurations when configured as a dedicated glucose monitoring device, such as the ability to make phone calls, camera functionality, the ability to utilize social networking applications, and so on.

Additionally, the computing device 108 may be representative of more than one device in accordance with the described techniques. In one or more scenarios, for instance, the computing device 108 may correspond to both a wearable device (e.g., a smart watch) and a mobile phone. In such scenarios, both of these devices may be capable of performing at least some of the same operations, such as to receive the glucose measurements 118 from the wearable glucose monitoring device 104, communicate them via the network 116 to the glucose monitoring platform 112, display information related to the glucose measurements 118, and so forth. Alternately or in addition, different devices may have different capabilities that other devices do not have or that are limited through computing instructions to specified devices.

In the scenario where the computing device 108 corresponds to a separate smart watch and a mobile phone, for instance, the smart watch may be configured with various sensors and functionality to measure a variety of physiological markers (e.g., heartrate, breathing, rate of blood flow, and so on) and activities (e.g., steps) of the person 102. In this scenario, the mobile phone may not be configured with these sensors and functionality, or it may include a limited amount of that functionality—although in other scenarios a mobile phone may be able to provide the same functionality. Continuing with this particular scenario, the mobile phone may have capabilities that the smart watch does not have, such as a camera to capture images of meals used to predict future glucose levels and an amount of computing resources (e.g., battery and processing speed) that enables the mobile phone to more efficiently carry out computations in relation to the glucose measurements 118. Even in scenarios where a smart watch is capable of carrying out such computations, computing instructions may limit performance of those computations to the mobile phone so as not to burden both devices and to utilize available resources efficiently. To this extent, the computing device 108 may be configured in different ways and represent different numbers of devices than discussed herein without departing from the spirit and scope of the described techniques.

As mentioned above, the computing device 108 communicates the glucose measurements 118 to the glucose monitoring platform 112. In the illustrated environment 100, the glucose measurements 118 are shown stored in storage device 120 of the glucose monitoring platform 112. The storage device 120 may represent one or more databases and also other types of storage capable of storing the glucose measurements 118. The storage device 120 also stores a variety of other data. In accordance with the described techniques, for instance, the person 102 corresponds to a user of at least the glucose monitoring platform 112 and may also be a user of one or more other, third party service providers. To this end, the person 102 may be associated with a username and be required, at some time, to provide authentication information (e.g., password, biometric data, a telemedicine service, and so forth) to access the glucose monitoring platform 112 using the username. This information, along with other information about the user, may be maintained in the storage device 120, including, for example, demographic information describing the person 102, information about a health care provider, payment information, prescription information, determined health indicators, user preferences, account information for other service provider systems (e.g., a service provider associated with a wearable, social networking systems, and so on), and so forth.

The storage device 120 also maintains data of the other users in the user population 110. Given this, the glucose measurements 118 in the storage device 120 include the glucose measurements from a glucose sensor of the wearable glucose monitoring device 104 worn by the person 102 and also include glucose measurements from glucose sensors of wearable glucose monitoring devices worn by persons corresponding to the other users in the user population 110. It follows also that the glucose measurements 118 of these other users are communicated by their respective devices via the network 116 to the glucose monitoring platform 112 and that these other users have respective user profiles with the glucose monitoring platform 112.

The data analytics platform 122 represents functionality to process the glucose measurements 118—alone and/or along with other data maintained in the storage device 120—to generate a variety of predictions, such as by using various machine learning models. Based on these predictions, the glucose monitoring platform 112 may provide notifications in relation to the predictions, such as alerts, recommendations, or other information based on the predictions. For instance, the glucose monitoring platform 112 may provide the notifications to the user, to a medical professional associated with the user, and so forth. Although depicted as separate from the computing device 108, portions or an entirety of the data analytics platform 122 may alternately or additionally be implemented at the computing device 108. The data analytics platform 122 may also generate these predictions using additional data obtained via the IoT 114.

It is to be appreciated that the IoT 114 represents various sources capable of providing data that describes the person 102 and the person 102's activity as a user of one or more service providers and activity with the real world. By way of example, the IoT 114 may include various devices of the user, e.g., cameras, mobile phones, laptops, and so forth. To this end, the IoT 114 may provide information about interaction of the user with various devices, e.g., interaction with web-based applications, photos taken, communications with other users, and so forth. The IoT 114 may also include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's surroundings, types of food stored in a refrigerator, types of food removed from a refrigerator, driving habits, and so forth. The IoT 114 may also include third parties to the glucose monitoring platform 112, such as medical providers (e.g., a medical provider of the person 102) and manufacturers (e.g., a manufacturer of the wearable glucose monitoring device 104, the insulin delivery system 106, or the computing device 108) capable of providing medical and manufacturing data, respectively, that can be leveraged by the data analytics platform 122. Certainly, the IoT 114 may include devices and sensors capable of providing a wealth of data for use in connection with glucose prediction using machine learning and time series glucose measurements without departing from the spirit or scope of the described techniques. In the context of measuring glucose, e.g., continuously, and obtaining data describing such measurements, consider the following discussion of FIG. 2.

Figure 2:
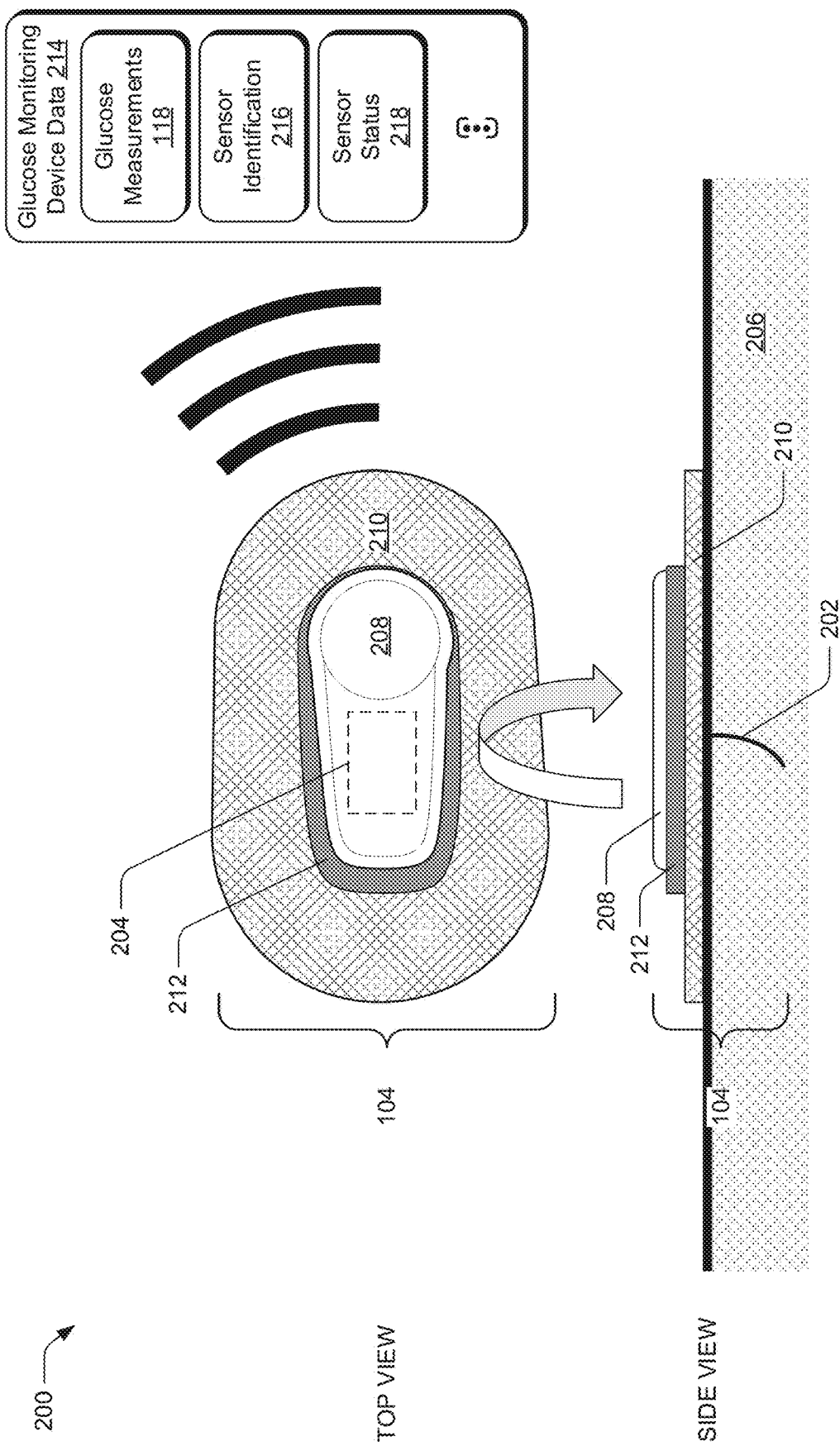
FIG. 2 depicts an example of the wearable glucose monitoring device of FIG. 1 in greater detail.

FIG. 2 depicts an example implementation 200 of the wearable glucose monitoring device 104 of FIG. 1 in greater detail. In particular, the illustrated example 200 includes a top view and a corresponding side view of the wearable glucose monitoring device 104.

The wearable glucose monitoring device 104 is illustrated to include a sensor 202 and a sensor module 204. In the illustrated example 200, the sensor 202 is depicted in the side view having been inserted subcutaneously into skin 206, e.g., of the person 102. The sensor module 204 is depicted in the top view as a dashed rectangle. The wearable glucose monitoring device 104 also includes a transmitter 208 in the illustrated example 200. Use of the dashed rectangle for the sensor module 204 indicates that it may be housed or otherwise implemented within a housing of the transmitter 208. In this example 200, the wearable glucose monitoring device 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 via the attachment mechanism 212. Additionally or alternatively, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate applicator (not shown). This application assembly may also be removed by peeling the adhesive pad 210 off of the skin 206. It is to be appreciated that the wearable glucose monitoring device 104 and its various components as illustrated are simply one example form factor, and the wearable glucose monitoring device 104 and its components may have different form factors without departing from the spirit or scope of the described techniques.

In operation, the sensor 202 is communicatively coupled to the sensor module 204 via at least one communication channel which can be a "wireless" connection or a "wired" connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques.

In another example, the sensor 202 (or an additional sensor of the wearable glucose monitoring device 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the wearable glucose monitoring device 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 118 based on the communications with the sensor 202 that are indicative of the above-discussed changes. Based on these communications from the sensor 202, the sensor module 204 is further configured to generate glucose monitoring device data 214. The glucose monitoring device data 214 is a communicable package of data that includes at least one glucose measurement 118. Alternately or additionally, the glucose monitoring device data 214 includes other data, such as multiple glucose measurements 118, sensor identification 216, sensor status 218, and so forth. In one or more implementations, the glucose monitoring device data 214 may include other information such as one or more of temperatures that correspond to the glucose measurements 118 and measurements of other analytes. It is to be appreciated that the glucose monitoring device data 214 may include a variety of data in addition to at least one glucose measurement 118 without departing from the spirit or scope of the described techniques.

In operation, the transmitter 208 may transmit the glucose monitoring device data 214 wirelessly as a stream of data to the computing device 108. Alternately or additionally, the sensor module 204 may buffer the glucose monitoring device data 214 (e.g., in memory of the sensor module 204) and cause the transmitter 208 to transmit the buffered glucose monitoring device data 214 at various intervals, e.g., time intervals (every second, every thirty seconds, every minute, every five minutes, every hour, and so on), storage intervals (when the buffered glucose monitoring device data 214 reaches a threshold amount of data or a number of instances of glucose monitoring device data 214), and so forth.

In addition to generating the glucose monitoring device data 214 and causing it to be communicated to the computing device 108, the sensor module 204 may include additional functionality in accordance with the described techniques. This additional functionality may include generating predictions of glucose levels of the person 102 in the future and communicating notifications based on the predictions, such as by communicating warnings when the predictions indicate that the person 102's level of glucose is likely to be dangerously low in the near future. This computational ability of the sensor module 204 may be advantageous especially where connectivity to services via the network 116 is limited or non-existent. In this way, a person may be alerted to a dangerous condition without having to rely on connectivity, e.g., to the Internet. This additional functionality of the sensor module 204 may also include calibrating the sensor 202 initially or on an ongoing basis as well as calibrating any other sensors of the wearable glucose monitoring device 104.

With respect to the glucose monitoring device data 214, the sensor identification 216 represents information that uniquely identifies the sensor 202 from other sensors, such as other sensors of other wearable glucose monitoring devices 104, other sensors implanted previously or subsequently in the skin 206, and so on. By uniquely identifying the sensor 202, the sensor identification 216 may also be used to identify other aspects about the sensor, 202 such as a manufacturing lot of the sensor 202, packaging details of the sensor 202, shipping details of the sensor 202, and so on. In this way, various issues detected for sensors manufactured, packaged, and/or shipped in a similar manner as the sensor 202 may be identified and used in different ways, e.g., to calibrate the glucose measurements 118, to notify users to change defective sensors or dispose of them, to notify manufacturing facilities of machining issues, and so forth.

The sensor status 218 represents a state of the sensor 202 at a given time, e.g., a state of the sensor at a same time one of the glucose measurements 118 is produced. To this end, the sensor status 218 may include an entry for each of the glucose measurements 118, such that there is a one-to-one relationship between the glucose measurements 118 and statuses captured in the sensor status 218 information. Generally speaking, the sensor status 218 describes an operational state of the sensor 202. In one or more implementations, the sensor module 204 may identify one of a number of predetermined operational states for a given glucose measurement 118. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation, e.g., within a threshold of an expected time, within a threshold of expected signal strength, an environmental temperature is within a threshold of suitable temperatures to continue operation as expected, and so forth. The predetermined states may also include operational states that indicate one or more characteristics of the sensor 202's communications are outside of normal activity and may result in potential errors in the glucose measurements 118.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has rolled (e.g., in bed) onto the wearable glucose monitoring device 104, and so forth. The sensor status 218 may indicate a variety of aspects about the sensor 202 and the wearable glucose monitoring device 104 without departing from the spirit or scope of the described techniques.

Having considered an example environment and example wearable glucose monitoring device, consider now a discussion of some example details of the techniques for glucose prediction using machine learning and time series glucose measurements in a digital medium environment in accordance with one or more implementations.

Glucose Prediction

Figure 3:
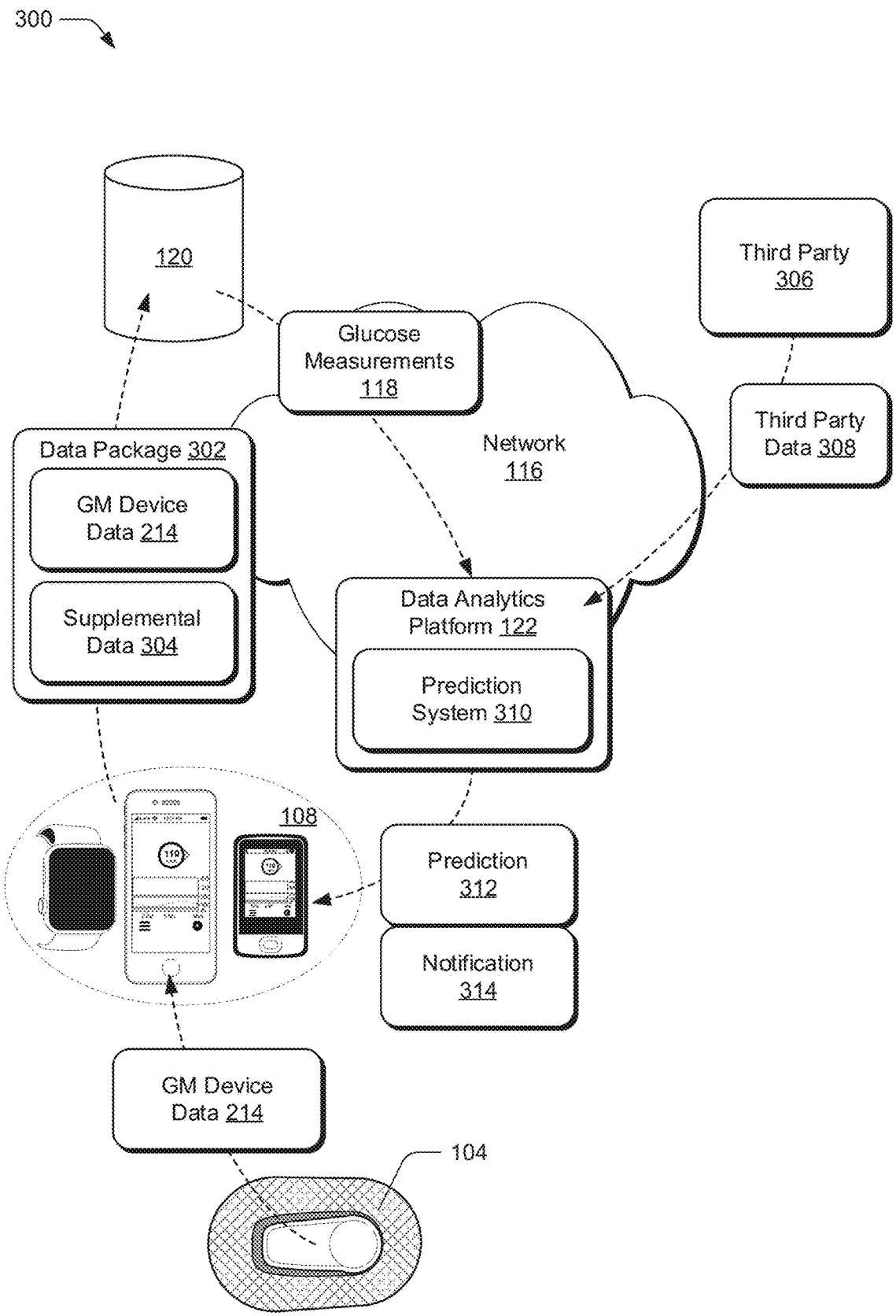
FIG. 3 depicts an example implementation in which glucose monitoring device data, including glucose measurements, is routed to different systems in connection with glucose prediction.

FIG. 3 depicts an example implementation 300 in which glucose monitoring device data, including glucose measurements, is routed to different systems in connection with glucose prediction.

The illustrated example 300 includes from FIG. 1 the wearable glucose monitoring device 104 and examples of the computing device 108. The illustrated example 300 also includes the data analytics platform 122 and the storage device 120, which, as discussed above, stores the glucose measurements 118. In this example 300, the wearable glucose monitoring device 104 is depicted transmitting the glucose monitoring device data 214 to the computing device 108. As discussed above in relation to FIG. 2, the glucose monitoring device data 214 includes the glucose measurements 118 along with other data. The wearable glucose monitoring device 104 may transmit the glucose monitoring device data 214 to the computing device 108 in a variety of ways.

The illustrated example 300 also includes data package 302. The data package 302 may include the glucose monitoring device data 214 (e.g., the glucose measurements 118, the sensor identification 216, and the sensor status 218) and supplemental data 304, or portions thereof. In this example 300, the data package 302 is depicted being routed from the computing device 108 to the storage device 120 of the glucose monitoring platform 112. Broadly speaking, the computing device 108 includes functionality to generate the supplemental data 304 based, at least in part, on the glucose monitoring device data 214. The computing device 108 also includes functionality to package the supplemental data 304 together with the glucose monitoring device data 214 to form the data package 302 and communicate the data package 302 to the glucose monitoring platform 112 for storage in the storage device 120, e.g., via the network 116. It is to be appreciated, therefore, that the data package 302 may include data collected by the wearable glucose monitoring device 104 (e.g., the glucose measurements 118 sensed by the sensor 202) as well as supplemental data 304 generated by the computing device 108 that acts as an intermediary between the wearable glucose monitoring device 104 and the glucose monitoring platform 112, such as a mobile phone or a smart watch of the user.

With respect to the supplemental data 304, the computing device 108 may generate a variety of supplemental data to supplement the glucose monitoring device data 214 included in the data package 302. In accordance with the described techniques, the supplemental data 304 may describe one or more aspects of a user's context, such that correspondences of the user's context with glucose monitoring device data 214 (e.g., the glucose measurements 118) can be identified. By way of example, the supplemental data 304 may describe user interaction with the computing device 108, and include, for instance, data extracted from application logs describing interaction (e.g., selections made, operations performed) for particular applications. The supplemental data 304 may also include clickstream data describing clicks, taps, and presses performed in relation to input/output interfaces of the computing device 108. As another example, the supplemental data 304 may include gaze data describing where a user is looking (e.g., in relation to a display device associated with the computing device 108 or when the user is looking away from the device), voice data describing audible commands and other spoken phrases of the user or other users (e.g., including passively listening to users), device data describing the device (e.g., make, model, operating system and version, camera type, apps the computing device 108 is running), and so on.

The supplemental data 304 may also describe other aspects of a user's context, such as environmental aspects including, for example, a location of the user, a temperature at the location (e.g., outdoor generally, proximate the user using temperature sensing functionality), weather at the location, an altitude of the user, barometric pressure, context information obtained in relation to the user via the IoT 114 (e.g., food the user is eating, a manner in which a user is using sporting equipment, clothes the user is wearing), and so forth. The supplemental data 304 may also describe health-related aspects detected about a user including, for example, steps, heart rate, perspiration, a temperature of the user (e.g., as detected by the computing device 108), and so forth. To the extent that the computing device 108 may include functionality to detect, or otherwise measure, some of the same aspects as the wearable glucose monitoring device 104, the data from these two sources may be compared, e.g., for accuracy, fault detection, and so forth. The above-discussed types of the supplemental data 304 are merely examples and the supplemental data 304 may include more, fewer, or different types of data without departing from the spirit or scope of the techniques described herein.

Regardless of how robustly the supplemental data 304 describes a context of a user, the computing device 108 may communicate the data packages 302, containing the glucose monitoring device data 214 and the supplemental data 304, to the glucose monitoring platform 112 for processing at various intervals. In one or more implementations, the computing device 108 may stream the data packages 302 to the glucose monitoring platform 112 substantially in real-time, e.g., as the wearable glucose monitoring device 104 provides the glucose monitoring device data 214 continuously to the computing device 108. The computing device 108 may alternately or additionally communicate one or more of the data packages 302 to the glucose monitoring platform 112 at a predetermined interval, e.g., every second, every 30 seconds, every hour, and so on.

Although not depicted in the illustrated example 300, the glucose monitoring platform 112 may process these data packages 302 and cause at least some of the glucose monitoring device data 214 and the supplemental data 304 to be stored in the storage device 120. From the storage device 120, this data may be provided to, or otherwise accessed by, the data analytics platform 122, e.g., to generate predictions of upcoming glucose levels, as described in more detail below.

In one or more implementations, the data analytics platform 122 may also ingest data from a third party 306 (e.g., a third party service provider) for use in connection with generating predictions of upcoming glucose levels. By way of example, the third party 306 may produce its own, additional data, such as via devices that the third party 306 manufactures and/or deploys, e.g., wearable devices. The illustrated example 300 includes third party data 308, which is shown being communicated from the third party 306 to the data analytics platform 122 and represents this additional data produced by or otherwise communicated from the third party 306.

As mentioned above, the third party 306 may manufacture and/or deploy associated devices. Additionally or alternately, the third party 306 may obtain data through other sources, such as corresponding applications. This data may thus include user-entered data entered via corresponding third party applications, e.g., social networking applications, lifestyle applications, and so forth. Given this, the data produced by the third party 306 may be configured in various ways, including as proprietary data structures, text files, images obtained via mobile devices of users, formats indicative of text entered to exposed fields or dialog boxes, formats indicative of option selections, and so forth.

The third party data 308 may describe various aspects related to one or more services provided by a third party without departing from the spirit or scope of the described techniques. The third party data 308 may include, for instance, application interaction data which describes usage or interaction by users with a particular application provided by the third party 306. Generally, the application interaction data enables the data analytics platform 122 to determine usage, or an amount of usage, of a particular application by users of the user population 110. Such data, for example, may include data extracted from application logs describing user interactions with a particular application, clickstream data describing clicks, taps, and presses performed in relation to input/output interfaces of the application, and so forth. In one or more implementations, the data analytics platform 122 may thus receive the third party data 308 produced or otherwise obtained by the third party 306.

The data analytics platform 122 is illustrated with prediction system 310. In accordance with the described systems, the prediction system 310 is configured to generate predictions 312 based on the glucose measurements 118. Specifically, the prediction system 310 is configured to generate predictions 312 of glucose measurements over an upcoming time interval, such as a glucose trace for the upcoming time interval. As discussed in more detail below, these predictions 312 are based on the glucose measurements 118 that have been sequenced according to timestamps to form time series glucose measurements, e.g., glucose traces. In one or more implementations, for instance, the prediction system 310 may generate predictions 312 based on both the glucose measurements 118 and additional data, where the additional data may include one or more portions of the glucose monitoring device data 214 additional to the glucose measurements 118, the supplemental data 304, the third party data 308, data from the IoT 114, and so forth. As discussed below, the prediction system 310 may generate such predictions 312 by using one or more machine learning models. These models may be trained or otherwise built using the glucose measurements 118 and additional data obtained from the user population 110.

Based on the generated predictions 312, the data analytics platform 122 may also generate notification 314. In scenarios where the prediction system 310 is implemented at least partially at the computing device 108, an application of the glucose monitoring platform 112 on the computing device may generate the notification 314 based on the generated predictions 312. The notification 314, for instance, may alert a user about an upcoming adverse health condition, such as that the user is likely to experience dysglycemia (i.e., hyper- or hypoglycemia) absent a mitigating behavior (e.g., eating, taking insulin, exercise, and so forth). The notification 314 may also provide support for deciding how to treat diabetes, such as by recommending a user perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on.

In such scenarios, a communication interface (not shown) of the data analytics platform 122 communicates the prediction 312 and/or the notification 314 for output via the computing device 108, e.g., via an application of the glucose monitoring platform 112. The communication interface may be configured with various communicative couplings (wired and/or wireless) via which data can be communicated over networks. This communication interface may also be implemented using a variety of software, firmware, and hardware to cause transmission and receipt of such data. In any case, is to be appreciated that either or both of the prediction 312 and the notification 314 may be communicated to the computing device 108. Additionally or alternately the prediction 312 and/or the notification 314 may be routed to a decision support platform and/or a validation platform, e.g., before the prediction 312 and/or notification 314 are allowed to be delivered to the computing device 108. In the context of generating one or more predictions, consider the following discussion of FIG. 4.

Figure 4:
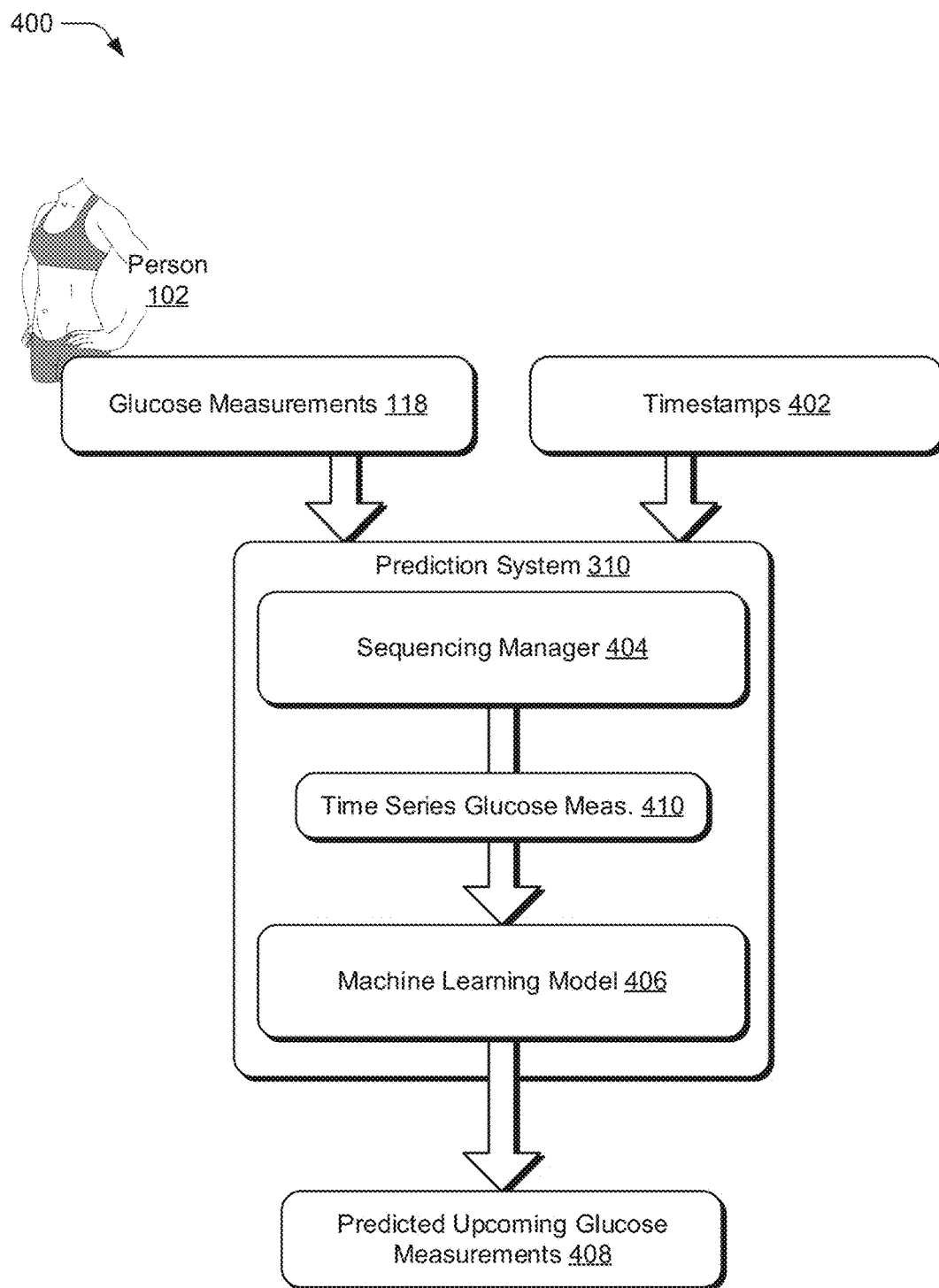
FIG. 4 depicts an example implementation of the prediction system of FIG. 3 in greater detail in which upcoming glucose measurements are predicted using machine learning.

FIG. 4 depicts an example implementation 400 of the prediction system 310 of FIG. 3 in greater detail in which upcoming glucose measurements are predicted using machine learning.

In the illustrated example 400, the prediction system 310 is shown obtaining the glucose measurements 118 and timestamps 402, e.g., from the storage device 120. Here, the glucose measurements 118 may correspond to the person 102. Additionally, each of the glucose measurements 118 corresponds to one of the timestamps 402. In other words, there may be a one-to-one relationship between glucose measurements 118 and timestamps 402, such that there is a corresponding timestamp 402 for each individual glucose measurement 118. In one or more implementations, the glucose monitoring device data 214 may include a glucose measurement 118 and a corresponding timestamp 402. Accordingly, the corresponding timestamp 402 may be associated with the glucose measurement 118 at the wearable glucose monitoring device 104 level, e.g., in connection with producing the glucose measurement 118. Regardless of how a timestamp 402 is associated with a glucose measurement 118—or which device associates a timestamp 402 with a glucose measurement 118—each of the glucose measurements 118 has a corresponding timestamp 402.

In this example 400, the prediction system 310 is depicted including sequencing manager 404 and machine learning model 406, which are configured to generate predicted upcoming glucose measurements 408 based on the glucose measurements 118 and the timestamps 402. Although the prediction system 310 is depicted including these two components, it is to be appreciated that the prediction system 310 may have more, fewer, and/or different components to generate the predicted upcoming glucose measurements 408 based on the glucose measurements 118 and the timestamps 402 without departing from the spirit or scope of the described techniques.

Broadly speaking, the sequencing manager 404 is configured to generate time series glucose measurements 410 based on the glucose measurements 118 and the timestamps 402. Although the glucose measurements 118 may generally be received in order, e.g., by the glucose monitoring platform 112 from the wearable glucose monitoring device 104 and/or the computing device 108, in some instances, one or more of the glucose measurements 118 may not be received in a same order in which the glucose measurements 118 are produced. For instance, packets with the glucose measurements 118 may be received out of order. Thus, the order of receipt may not chronologically match the order in which the glucose measurements 118 are produced by the wearable glucose monitoring device 104. In addition or alternately, the communications including one or more of the glucose measurements 118 may be corrupted. Indeed, there may be a variety of reasons why the glucose measurements 118, as obtained by the prediction system 310, are not entirely in time order.

To generate the time series glucose measurements 410, the sequencing manager 404 determines a time-ordered sequence of the glucose measurements 118 according to the respective timestamps 402. Due to corruption and communication errors, the glucose measurements 118 obtained by the prediction system 310 may not only be out of time order but may also be missing one or more measurements—there may be gaps in the time-ordered sequence where one or more measurements are expected. In these instances, the sequencing manager 404 interpolates the missing glucose measurements and incorporates them into the time-ordered sequence.

The sequencing manger 404 outputs the time-ordered sequence of the glucose measurements 118 as the time series glucose measurements 410. The time series glucose measurements 410 may be configured as or otherwise referred to as a "glucose trace." In contrast to the predicted upcoming glucose measurements 408, the time series glucose measurements 410 are a trace of glucose measurements that have been observed by a wearable glucose monitoring device, such as by the wearable glucose monitoring device 104 worn by the person 102. Glucose measurements observed in this way contrast with glucose measurements predicted, e.g., by the machine learning model 406.

For example, the time series glucose measurements 410 may be a trace of the glucose measurements 118 observed for the person 102 over a previous 12 hours from a time the prediction is initiated. In contrast, the predicted upcoming glucose measurements 408 may be configured as an additional trace of glucose measurements spanning from a time the prediction is initiated to a time 30 minutes into the future. It is to be appreciated that the time series glucose measurements 410 and the predicted upcoming glucose measurements 408 may correspond to different time intervals than 12 hours and 30 minutes, respectively, without departing from the spirit or scope of the described techniques.

In accordance with the described techniques, the time series glucose measurements 410 are provided as input to the machine learning model 406. Responsive to receiving the time series glucose measurements 410 as input, the machine learning model 406 is configured to generate and output the predicted upcoming glucose measurements 408. Although the machine learning model 406 is generally described as generating the predicted upcoming glucose measurements 408 from input of the time series glucose measurements 410, in one or more implementations, the machine learning model 406 may receive additional inputs in order to generate the predicted upcoming glucose measurements 408. By way of example, the machine learning model 406 may receive as input a patient-specific correction factor (e.g., specific to the person 102) along with the time series glucose measurements 410. The prediction system 310 may determine a patient-specific correction factor for the person 102 based on historical glucose measurements 118 of the person 102, device data of the wearable glucose monitoring device 104 and other previously worn glucose monitoring devices, interaction data describing interactions of the person 102 with the wearable glucose monitoring device 104 and an application of the glucose monitoring platform 112, and health (or status) of the person 102's wearable glucose monitoring device 104, to name just a few. The machine learning model 406 may receive other data as input without departing from the spirit or scope of the described techniques.

Regardless of the particular data received as input, the machine learning model 406 is trained to output the predicted upcoming glucose measurements 408. By way of example, the machine learning model 406 may be trained, or an underlying model may be learned, based on one or more training approaches and using historical time series glucose measurements, such as time series glucose measurements generated from the glucose measurements 118 of the user population 110. Such training may utilize a large amount of training data generated from the glucose measurements 118 of the user population 110, such as by forming training data comprising vectors of users' individual glucose measurements 118 over fixed time intervals (e.g., hours, days, or weeks) from the user population 110 data maintained in the storage device 120. This data may be used, in part, for testing and validation of the machine learning model 406. Training the machine learning model 406 is discussed in more detail in relation to FIG. 8.

In contrast to conventional glucose prediction approaches, the machine learning model 406 is configured as a non-linear model. Conventional approaches to glucose prediction may model glucose using linear models, such as with autoregressive linear models. Although such linear models may be capable of describing time-varying processes, the output of the models is linearly dependent on previous values. This can result in glucose predictions that have significant time delays in relation to actual, observed glucose measurements.

By way of example, a conventionally configured linear model may output a prediction that is intended to indicate a person's glucose measurement 30 minutes into the future from a current time. However, the person's observed glucose may correspond to the predicted measurement a mere five minutes into the future. To this end, the conventionally configured linear model's prediction is 25 minutes delayed—the predictive horizon of the conventional model thus fails to match the person's actual glucose. Additionally, linear models may generate less accurate predictions of upcoming glucose measurements than a non-linear model as described herein. This is because linear models may not be able to account for some patterns observed in historical data, which can be captured using non-linear approaches. Failure of the predictive horizon to match actual glucose and less accurate predictions may render glucose predictions generated by conventional systems unsuitable for various applications, such as for prescribing actions to mitigate dangerously (and rapidly) changing glucose levels.

Instead, the machine learning model 406 may be configured as a non-linear model or as an ensemble of models that includes one or more non-linear models. The machine learning model 406 may be configured as a generative model, which extrapolates a sequence of glucose measurements, e.g., multiple hours into the future. Non-linear and generative machine learning models may include, for instance, neural networks (e.g., recurrent neural networks such as long-short term memory (LSTM) network), state machines, Markov chains (e.g., hidden Markov models), Monte Carlo methods, and particle filters, to name just a few. Generally speaking, these types of models may be configured to learn patterns in data that correspond to long-term trends, enabling them to learn dynamics of glucose measurements through sequence recognition. It is to be appreciated that the machine learning model 406 may be configured as or otherwise include one or more different types of non-linear machine learning models without departing from the spirit or scope of the described techniques. As one example of a non-linear machine learning model, consider FIG. 5.

Figure 5:
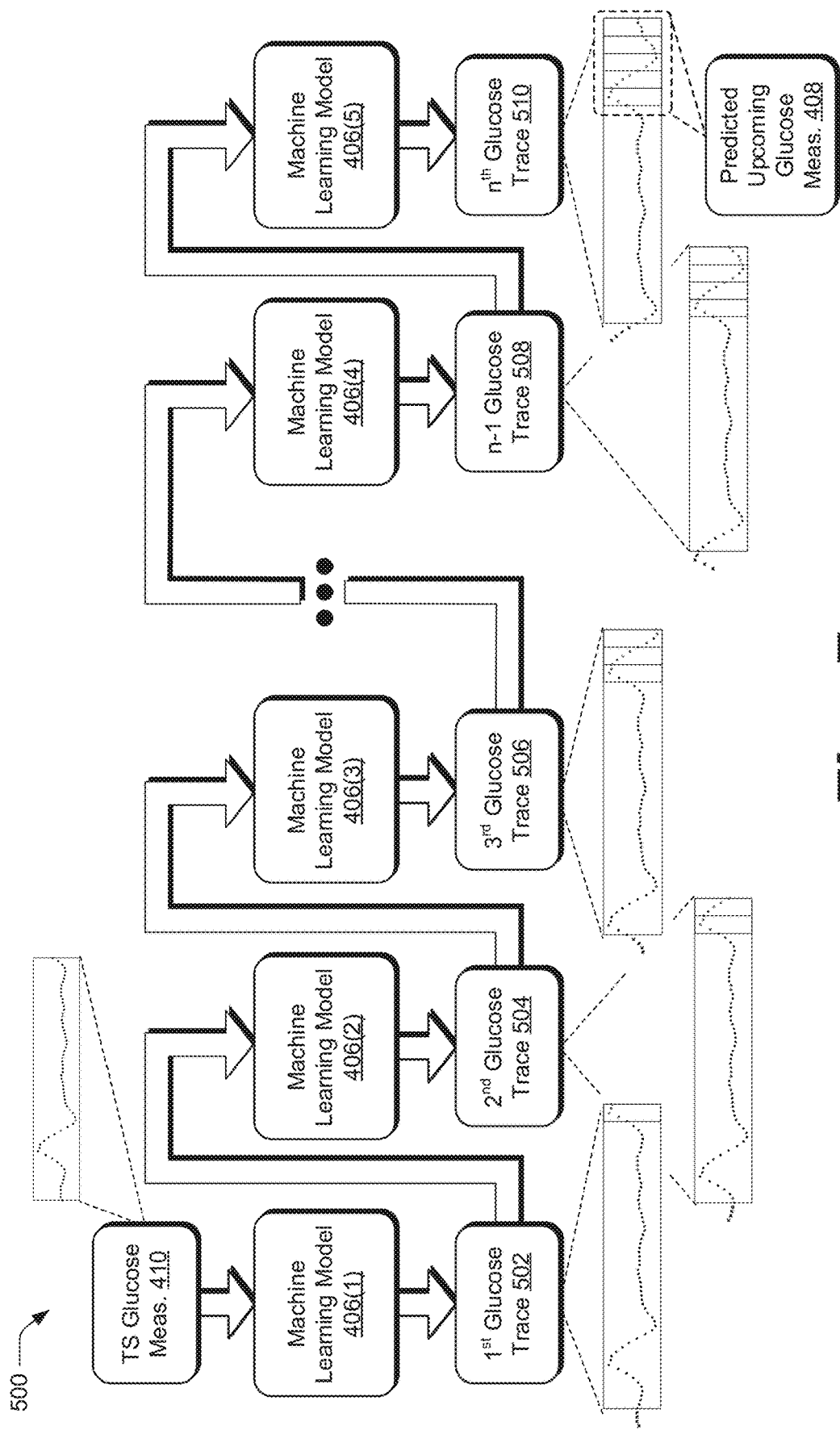
FIG. 5 depicts an example implementation in which a machine learning model predicts upcoming glucose measurements with iterative predictions.

FIG. 5 depicts an example implementation 500 in which a machine learning model predicts upcoming glucose measurements with iterative predictions.

The illustrated example 500 includes the time series glucose measurements 410 and the predicted upcoming glucose measurements 408. Here, the time series glucose measurements 410 and the predicted upcoming glucose measurements 408 are depicted as input to and output from, respectively, steps of the machine learning model 406. In particular, the illustrated example 500 includes a plurality of steps of the machine learning model 406(1)-(5). This may represent a scenario in which the machine learning model 406 is configured as a recurrent neural network, such as an LSTM network. In scenarios where the machine learning model 406 is configured as an LSTM network, for example, the steps of the machine learning model 406(1)-(5) represent repeating modules of the network.

The illustrated example 500 also includes glucose traces 502-510, including a first glucose trace 502, a second glucose trace 504, a third glucose trace 506, an $(n-1)^{th}$ glucose trace 508, and an $n^{th}$ glucose trace 510 as well as visualizations of those glucose traces and a visualization of the time series glucose measurements 410. The visualizations of the time series glucose measurements 410 and the glucose traces 502-510 are depicted in greater detail in FIGS. 6 and 7. The discussion of the illustrated example 500 refers to details of the visualizations as depicted in FIGS. 6 and 7.

Figure 6:
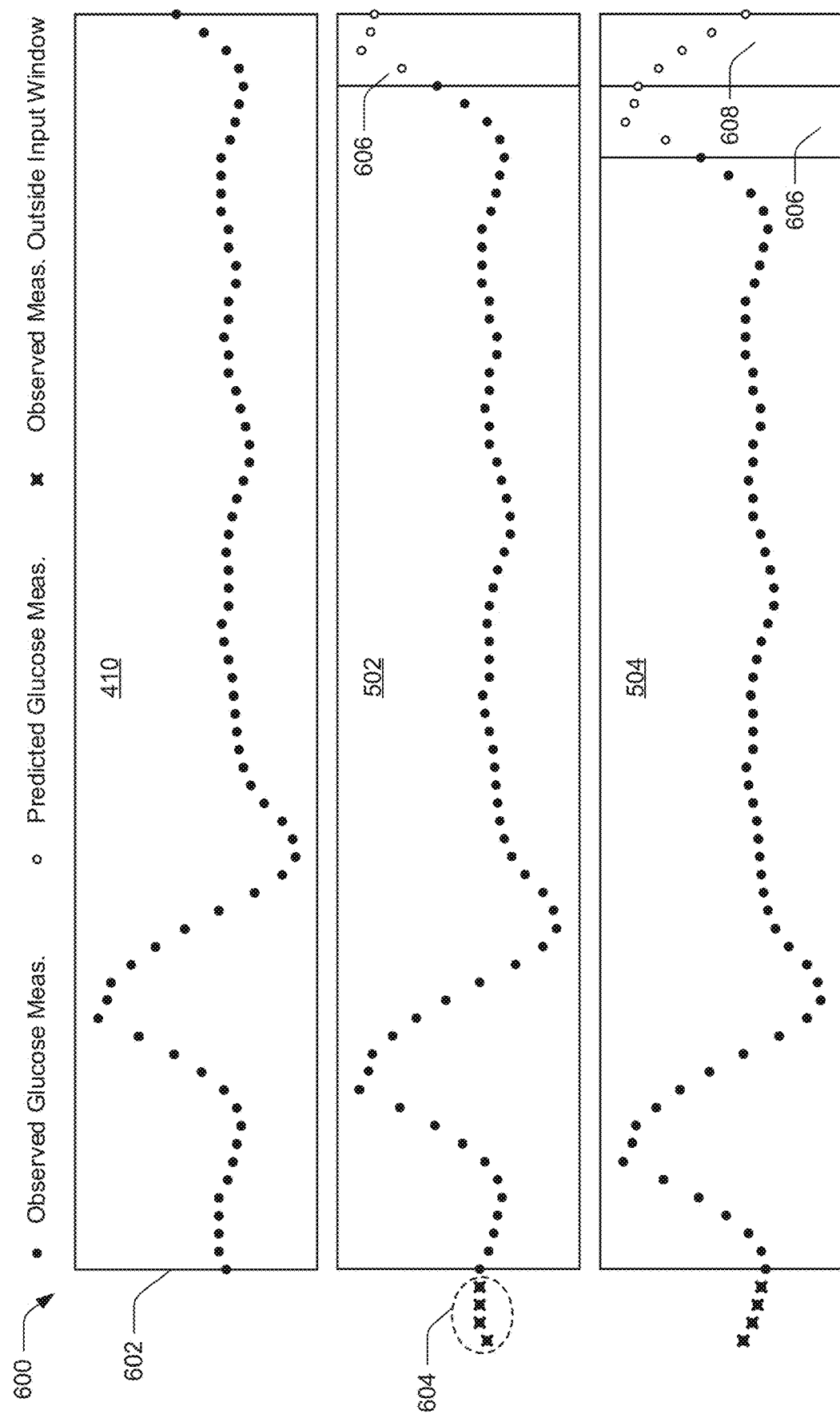
FIG. 6 depicts example visualizations of observed and predicted glucose traces.
Figure 7:
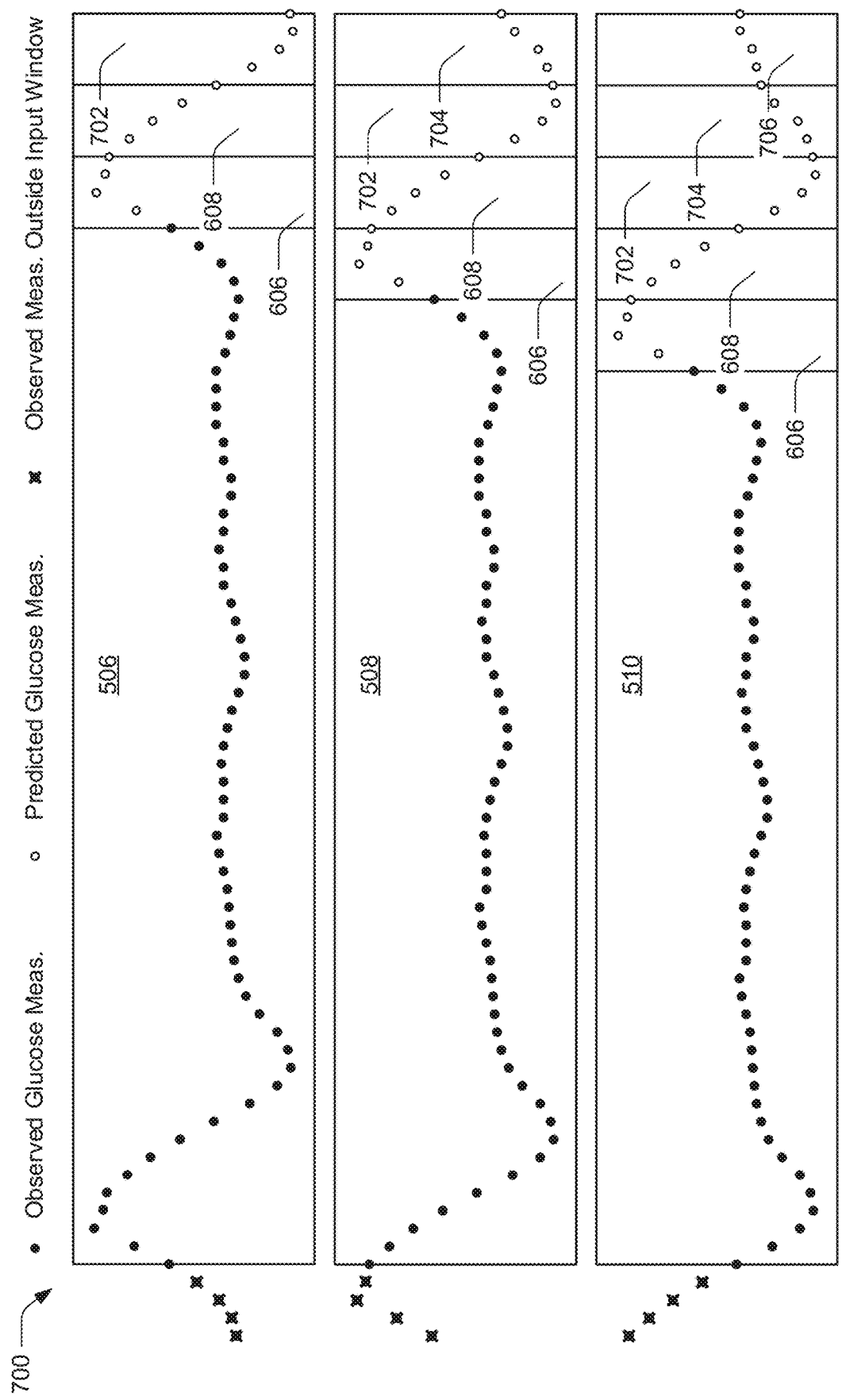
FIG. 7 depicts example visualizations of additional predicted glucose traces.

Specifically, FIG. 6 depicts example visualizations 600 of observed and predicted glucose traces, including visualizations of the time series glucose measurements 410, the first glucose trace 502, and the second glucose trace 504. FIG. 7 depicts example visualizations 700 of predicted glucose traces, including visualizations of the third glucose trace 506, the $(n-1)^{th}$ glucose trace 508, and the $n^{th}$ glucose trace 510.

In the illustrated example 500, the step of the machine learning model 406(1) is shown receiving the time series glucose measurements 410 as input. With reference to the example visualizations 600, the visualization of the time series glucose measurements 410 includes a plurality of points that represent observed glucose measurements and that are disposed within input window 602. This represents that the glucose measurements represented by those points are input to the step of the machine learning model 406(1).

In the illustrated examples 600, 700 each of the visualizations includes the input window 602. Broadly speaking, the input window identifies which of the glucose measurements are predicted and which measurements are used as input to a next step. In these examples 600, 700, for instance, the glucose measurements within the input window 602 are input to a step of the machine learning model 406. In one or more implementations, the glucose measurements that are not within the input window 602 are not used as input to the next step. For instance, crossed-out points 604 of the first glucose trace 502 may not be input to the step of the machine learning model 406(2).

Although a size of the input window 602 is depicted remaining the same across the example visualizations 600, 700—representing that a same amount of time of time series glucose measurements is input to the machine learning model 406 at each step (e.g., 12 hours' worth of measurements)—it is to be appreciated that in one or more implementations, the input window 602 may not remain a same size. Instead, the input window may expand at each step to add an amount of time that corresponds to a timestep of the step's prediction. For example, if the time series glucose measurements 410 correspond to 12 hours' worth of data and the machine learning model 406 predicts five minutes' worth of glucose measurements at each step, then the first glucose trace 502 corresponds to 12 hours and 5 minutes' worth of data, and this 12 hours and 5 minutes' worth of data is input to the machine learning model at the second step. Continuing with this example, such input may produce the second glucose trace 504 as 12 hours and 10 minutes' worth of data.

Despite this and similar such approaches in various implementations, in the following discussion, an implementation is described in which the input window 602 remains a same size (e.g., in terms of amount of time's worth of time series glucose measurements). Also, it is to be appreciated that although a size of the input window 602 may remain the same across the different steps, different implementations may leverage an input window of a different size than discussed in the following, i.e., a different amount of time. In one or more implementations, the input window 602 may correspond to 12 hours' worth of glucose measurements, e.g., the time series glucose measurements 410 may correspond to 12 hours of the glucose measurements 118 that span back from a time at which generation of the predicted upcoming glucose measurements 408 is initiated. In other implementations, the input window 602 may have a different size, such that the time series glucose measurements 410 correspond, for example, to a last day's worth of glucose measurements, a last two days' worth of glucose measurements, a last 6 hours' worth of glucose measurements, or a last hour's worth of measurements, to name just a few.

Turning now to a stepwise discussion of the illustrated example 500. In this example 500, the first step of the machine learning model 406(1) is depicted receiving as input the time series glucose measurements 410. The first step of the machine learning model 406(1) is depicted outputting the first glucose trace 502. As depicted in the illustrated examples 600, the first glucose trace 502 includes a first timestep of glucose measurements 606. Generally speaking, each step of the machine learning model 406 is configured to predict a timestep of glucose measurements given an input window of glucose measurements. Accordingly, the first step machine learning model 406(1) predicts the first timestep of glucose measurements 606 based on the model's training and on one or more patterns in the time series glucose measurements 410. The first timestep of glucose measurements 606 includes glucose measurements predicted for a timestep that spans from initiation of the prediction to a subsequent time that corresponds to an amount of time of the timestep. The first step machine learning model 406(1) may append the first timestep of glucose measurements 606 to a terminal end of the time series glucose measurements 410 and also remove glucose measurements from a beginning of the time series, e.g., a timestep's worth of the glucose measurements. Alternately or additionally, the first step machine learning model 406 may simply predict the first timestep of glucose measurements 606 and additional logic (not shown) may perform the appending and removing. By predicting the first timestep of glucose measurements 606 and performing the appending and removing, the prediction system 310 forms the first glucose trace 502.

Consider an example of the predicting, appending, and removing where the input window corresponds to 12 hours and the timestep corresponds to 5 minutes. Here, the first step of the machine learning model 406(1) generates the first timestep of glucose measurements 606 as a 5-minute prediction of upcoming glucose measurements. This 5-minute prediction is appended to a terminal end of the time series glucose measurements 410, which is 12 hours of glucose measurements, thereby forming 12 hours and 5 minutes of glucose measurements. Then, 5 minutes of glucose measurements are removed from a beginning of this trace, forming the first glucose trace 502 as a 12-hour trace of glucose measurements. The first glucose trace 502, therefore, includes both observed glucose measurements and predicted glucose measurements. The first glucose trace 502 is then input to the second step of the machine learning model 406(2).

In this example 500, the second step of the machine learning model 406(2) is depicted outputting the second glucose trace 504. As depicted in the illustrated examples 600, the second glucose trace 504 includes the first timestep of glucose measurements 606 and a second timestep of glucose measurements 608. Here, the second step of the machine learning model 406(2) predicts the second timestep of glucose measurements 608 based on the model's training and on one or more patterns in the first glucose trace 502. The second timestep of glucose measurements 608 includes glucose measurements predicted for a timestep that spans from a time corresponding to one timestep's worth of time to a subsequent time corresponding to two timesteps' worth of time, e.g., glucose measurements for 5-10 minutes in the future.

In a similar manner as the preceding step, the second step of the machine learning model 406(2) may append the second timestep of glucose measurements 608 to a terminal end of the first glucose trace 502 and also remove glucose measurements from a beginning of the trace, e.g., a timestep's worth of the glucose measurements. Alternately or additionally, the above-mentioned additional logic (not shown) may perform the appending and removing. By predicting the second timestep of glucose measurements 608 and performing the appending and removing, the prediction system 310 forms the second glucose trace 504. The second glucose trace 504 is then input to the third step of the machine learning model 406(3).

In this example 500, the third step of the machine learning model 406(3) is depicted outputting the third glucose trace 506. As depicted in the illustrated examples 700, the third glucose trace 506 includes the first timestep of glucose measurements 606, the second timestep of glucose measurements 608, and a third timestep of glucose measurements 702. Here, the third step of the machine learning model 406(3) predicts the third timestep of glucose measurements 702 based on the model's training and on one or more patterns in the second glucose trace 504. The third timestep of glucose measurements 702 includes glucose measurements predicted for a timestep that spans from a time corresponding to two timesteps' worth of time to a subsequent time corresponding to three timesteps' worth of time, e.g., glucose measurements for 10-15 minutes in the future.

In a similar manner as with the preceding timesteps, the third step of the machine learning model 406(3) may append the third timestep of glucose measurements 702 to a terminal end of the second glucose trace 504 and also remove glucose measurements from a beginning of the trace, e.g., a timestep's worth of the glucose measurements. Alternately or additionally, the above-mentioned additional logic (not shown) may perform the appending and removing. By predicting the third timestep of glucose measurements 702 and performing the appending and removing, the prediction system 310 forms the third glucose trace 506. The third glucose trace 506 is then input to a next step of the machine learning model 406.

The illustrated example 500 includes ellipses to indicate that there may be one or more steps between the third step of the machine learning model 406(3) and the illustrated fourth step of the machine learning model 406(4). If the machine learning model 406 generates the predicted upcoming glucose measurements 408 for a 30-minute interval and the timestep of the prediction at each step is 5 minutes, then there are 6 steps of the machine learning model 406 (and only one not shown step between the third and fourth steps of the machine learning model 406(3),(4)). However, there may be more steps in one or more implementations, such as with 5-minute timesteps for an hour interval, 3-minute timesteps for a 30-minute interval, and so on. It is to be appreciated that there may be more or fewer steps than illustrated in this example 500 without departing from the spirit or scope of the techniques.

In any case, the fourth step of the machine learning model 406(4) receives a glucose trace from an immediately preceding step of the machine learning model 406 as input. Where there are n steps, for instance, the fourth step of the machine learning model 406(4) receives the $(n-2)^{th}$ glucose trace as input. Here, the fourth step of the machine learning model 406(4) is depicted outputting the $(n-1)^{th}$ glucose trace 508. As depicted in the illustrated examples 700, the $(n-1)^{th}$ glucose trace 508 includes the first timestep of glucose measurements 606, the second timestep of glucose measurements 608, the third timestep of glucose measurements 702, and an $(n-1)^{th}$ timestep of glucose measurements 704. Here, the fourth step of the machine learning model 406(4) predicts the $(n-1)^{th}$ timestep of glucose measurements 704 based on the model's training and on one or more patterns in a glucose trace from an immediately preceding step of the machine learning model 406.

Although not illustrated in the example visualizations 700, it is to be appreciated that if there are additional steps between the third and fourth steps of the machine learning model 406(3),(4), then there are also a corresponding number of additional timesteps of glucose measurements between the third timestep of glucose measurements 702 and the $(n-1)^{th}$ timestep of glucose measurements 704. The $(n-1)^{th}$ timestep of glucose measurements 704 includes glucose measurements predicted for a timestep that spans from a time corresponding to (n-2) timesteps' worth of time to a subsequent time corresponding to (n-1) timesteps' worth of time, e.g., glucose measurements for 20-25 minutes in the future.

In a similar manner as with the preceding timesteps, the fourth step of the machine learning model 406(4) may append the $(n-1)^{th}$ timestep of glucose measurements 704 to a terminal end of the immediately preceding glucose trace and also remove glucose measurements from a beginning of the trace, e.g., a timestep's worth of the glucose measurements. Alternately or additionally, the above-mentioned additional logic (not shown) may perform the appending and removing. By predicting the $(n-1)^{th}$ timestep of glucose measurements 704 and performing the appending and removing, the prediction system 310 forms the $(n-1)^{th}$ glucose trace 508. The $(n-1)^{th}$ glucose trace 508 is then input to a next step of the machine learning model 406, e.g., the illustrated fifth step of the machine learning model 406(5).

In this example 500, the fifth step of the machine learning model 406(5) is depicted outputting the $n^{th}$ glucose trace 510. As depicted in the illustrated examples 700, the $n^{th}$ glucose trace 510 includes the first timestep of glucose measurements 606, the second timestep of glucose measurements 608, the third timestep of glucose measurements 702, the $(n-1)^{th}$ timestep of glucose measurements 704, and an $n^{th}$ timestep of glucose measurements 706. Here, the fifth step of the machine learning model 406(5) predicts the $n^{th}$ timestep of glucose measurements 706 based on the model's training and on one or more patterns in the $(n-1)^{th}$ glucose trace 508. The $n^{th}$ timestep of glucose measurements 706 includes glucose measurements predicted for a timestep that spans from a time corresponding to (n-1) timesteps' worth of time to a subsequent time corresponding to n timesteps' worth of time, e.g., glucose measurements for 25-30 minutes in the future.

In a similar manner as with the preceding timesteps, the fifth step of the machine learning model 406(5) may append the $n^{th}$ timestep of glucose measurements 706 to a terminal end of the $(n-1)^{th}$ glucose trace 508 and also remove glucose measurements from a beginning of the trace, e.g., a timestep's worth of the glucose measurements. Alternately or additionally, the above-mentioned additional logic (not shown) may perform the appending and removing. By predicting the $n^{th}$ timestep of glucose measurements 706 and performing the appending and removing, the prediction system 310 forms the $n^{th}$ glucose trace 510.

The illustrated example 500 includes dashed lines extending from the predicted upcoming glucose measurements 408 and a dashed box around a portion of the $n^{th}$ glucose trace 510. Notably, the dashed box is illustrated around the first timestep of glucose measurements 606, the second timestep of glucose measurements 608, the third timestep of glucose measurements 702, the $(n-1)^{th}$ timestep of glucose measurements 704, and the $n^{th}$ timestep of glucose measurements 706. This represents that the predicted upcoming glucose measurements 408 may correspond to the combination of glucose measurements as predicted in those timesteps 606, 608, 702, 704, 706. The glucose measurements predicted in the timesteps 606, 608, 702, 704, 706 are distinguished from the glucose measurements of the time series glucose measurements 410 because the time series glucose measurements 410 are actually observed (e.g., produced by the wearable glucose monitoring device 104 while worn by the person 102) rather than predicted.

Although the machine learning model 406 may be configured to generate the predicted upcoming glucose measurements 408 iteratively, in timesteps as described in relation to FIGS. 6 and 7, in one or more implementations the machine learning model 406 may instead generate the predicted upcoming glucose measurements 408 in a single step—without using multiple iterations. In other words, rather than generate six five-minute timesteps of predictions—to predict 30 minutes' worth of predicted upcoming glucose measurements 408—the machine learning model 406 may instead simply generate a 30-minute prediction of the predicted upcoming glucose measurements 408 in a single step. For example, the machine learning model 406 may receive 12 hours' worth of the glucose measurements 118 as input and generate the 30 minutes' worth of the predicted upcoming glucose measurements 408 in one step—rather than doing so in iterations involving predicting, appending, and then inputting an augmented trace to the machine learning model 406.

In the illustrated examples 400, 500, the machine learning model 406 is depicted receiving the time series glucose measurements 410 as input only, and is not depicted receiving data describing other aspects that may impact a person's glucose in the future, such as insulin administered, carbohydrates consumed, exercise, and stress. Although in some implementations the machine learning model 406 may be limited to receiving time series glucose measurements 410 (and information about the time series glucose measurements 410 such as confidences), in one or more implementations, the machine learning model 406 may also receive data as input describing one or more other aspects that impact a person's glucose in the future.

Beyond insulin administration, carbohydrate consumption, exercise, and stress, further examples of aspects that may be indicative of a person's glucose in the future include accelerometer data of a mobile device or smart watch (e.g., indicating that that the person has viewed a user interface of the device and thus has likely seen an alert or information related to glucose measurements), application data (e.g., clickstream data describing user interfaces displayed and user interactions with applications via the user interfaces), environmental temperature, barometric pressure, and the presence or absence of various health conditions (e.g., pregnancy), to name just a few.

Figure 8:
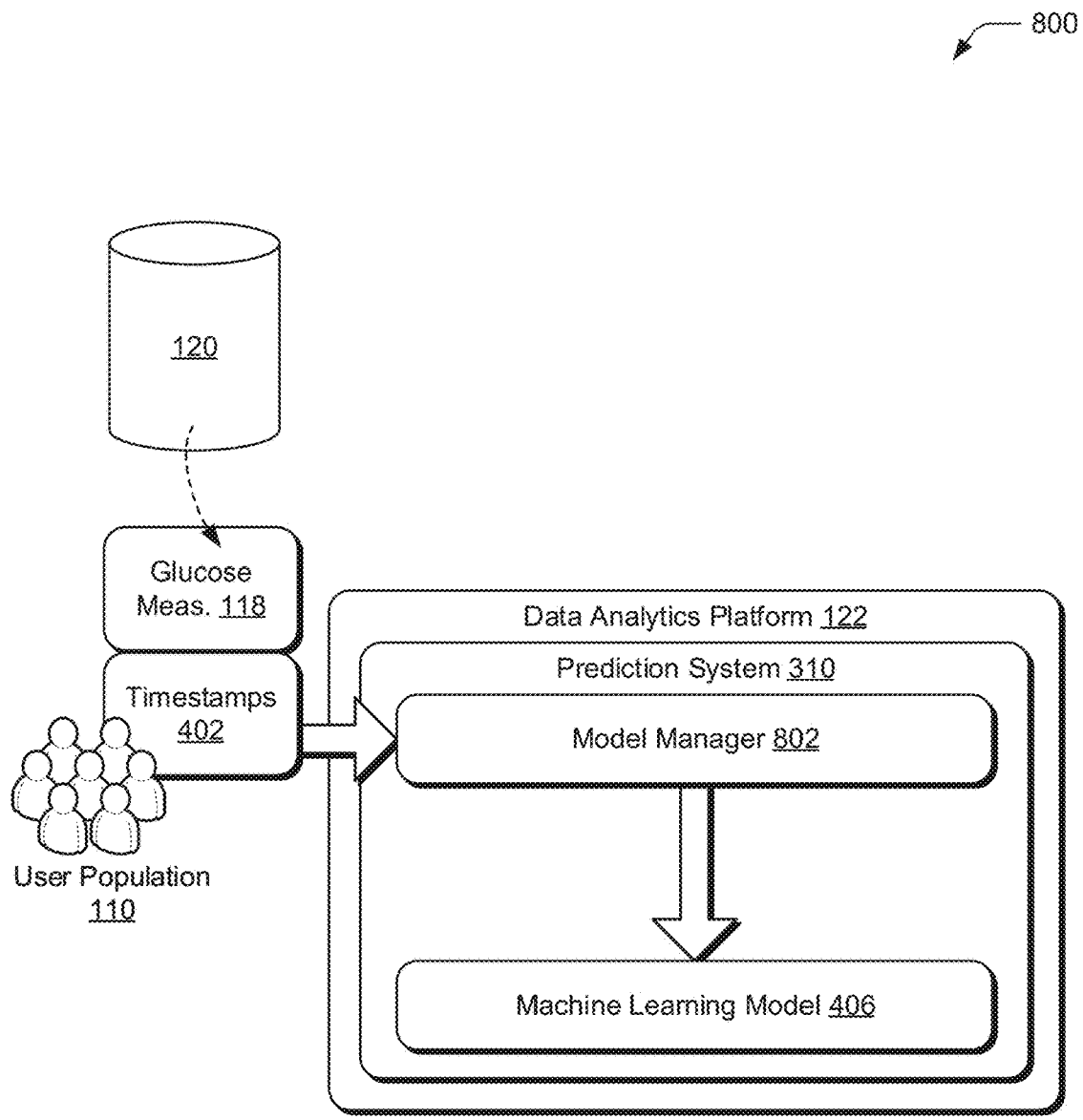
FIG. 8 depicts an example implementation of the prediction system of FIG. 3 in greater detail in which a machine learning model is trained to predict upcoming glucose measurements.

In the context of training the machine learning model 406 to predict upcoming glucose measurements based on time series of observed glucose measurements, consider the following discussion of FIG. 8.

FIG. 8 depicts an example implementation 800 of the prediction system 310 in greater detail in which a machine learning model is trained to predict upcoming glucose measurements. As in FIG. 3, the prediction system 310 is included as part of the data analytics platform 122, although in other scenarios the prediction system 310 may also or alternately be, in part or entirely, included in other devices such as the computing device 108.

In the illustrated example 800, the prediction system 310 includes model manager 802, which manages the machine learning model 406, which as mentioned above is configured as or includes one or more non-linear models, e.g., a recurrent neural network such as an LSTM. It is to be appreciated that the machine learning model 406 may be configured as or include other types of non-linear models without departing from the spirit or scope of the described techniques. These different machine learning models may be built or trained (or the model otherwise learned), respectively, using different algorithms due, at least in part, to different architectures. Accordingly, it is to be appreciated that the following discussion of the model manager 802's functionality is applicable to a variety of non-linear machine learning models. For explanatory purposes, however, the functionality of the model manager 802 will be described generally in relation to training a neural network.

Broadly speaking, the model manager 802 is configured to manage machine learning models, including the machine learning model 406. This model management includes, for example, building the machine learning model 406, training the machine learning model 406, updating this model, and so on. In one or more implementations, updating this model may include transfer learning to personalize the machine learning model 406—to personalize it from a state as trained with training data of the user population 110 to an updated state trained with additional training data or (update data) describing one or more aspects of the person 102 and/or describing one or more aspects of a subset of the user population 110 determined similar to the person 102. Specifically, the model manager 802 is configured to carry out model management using, at least in part, the wealth of data maintained in the storage device 120 of the glucose monitoring platform 112. As illustrated, this data includes the glucose measurements 118 and timestamps 402 of the user population 110. Said another way, the model manager 802 builds the machine learning model 406, trains the machine learning model 406 (or otherwise learns an underlying model), and updates this model using the glucose measurements 118 and the timestamps 402 of the user population 110. In implementations where the machine learning model 406 receives data in addition to time series glucose measurements as input, the model manager 802 also uses this other data of the user population 110 to build, train, and update the machine learning model 406.

Unlike conventional systems, the glucose monitoring platform 112 stores (e.g., in the storage device 120) or otherwise has access to glucose measurements 118 obtained using the wearable glucose monitoring device 104 for hundreds of thousands of users of the user population 110 (e.g., 500,000 or more). Moreover, these measurements are taken by sensors of the wearable glucose monitoring device 104 at a continuous rate. As a result, the glucose measurements 118 available to the model manager 802, for model building and training, number in the millions, or even billions. With such a robust amount of data, the model manager 802 can build and train the machine learning model 406 to accurately predict upcoming glucose of a person based on patterns in their observed glucose measurements.

Absent the robustness of the glucose monitoring platform 112's glucose measurements 118, conventional systems simply cannot build or train models to cover state spaces in a manner that suitably represents how patterns in glucose levels are indicative of future glucose levels. Failure to suitably cover these state spaces can result in glucose predictions that are inaccurate (e.g., in terms of an amount of glucose actually present in the person's blood or in terms of a timing of the prediction), which can lead to recommending unsafe actions or behaviors that could cause death. Given the gravity of generating inaccurate and untimely predictions, it is important to build the machine learning model 406 using an amount of glucose measurements 118 that is robust against rare events.

In one or more implementations, the model manager 802 generates training data to train the machine learning model 406. Initially, generating the training data includes forming training time series of glucose measurements from the glucose measurements 118 and the corresponding timestamps 402 of the user population 110. The model manager 802 may leverage the functionality of the sequencing manager 404 to form those training time series, for instance, in a similar manner as discussed in relation to forming the time series glucose measurements 410.

For each of the training time series, the model manager 802 may then generate an input portion of the training time series and an expected output portion of the training time series, i.e., a ground truth for comparison to the model's output during training. Accordingly, each instance of training data may include a training input portion and an expected output portion extracted from a training time series. The model manager 802 may generate those portions by segmenting a training time series, such as by selecting an input window's worth of the training time series for the input portion and also by using, as the expected output portion, a portion of the training time series that follows the selected portion subsequent in time. In scenarios where the machine learning model 406 generates predictions in steps, as discussed in relation to FIG. 5, the expected output portion may correspond to a timestep's worth of the training time series subsequent to the selected portion.

To demonstrate, consider again the example in which the machine learning model 406 is designed to receive 12 hours of time series glucose measurements as input and in which steps of the machine learning model 406 are trained to generate 5-minute predictions of upcoming glucose measurements. In this example, assume also that the training time series are 24 hours of time-ordered glucose measurements (24-hour glucose traces)—certainly the model manager 802 may use training time series of different lengths of time without departing from the spirit or scope of the described techniques. By way of example, a particular training time series may span from 12:00:00 PM on Apr. 8, 2020 to 12:00:00 PM on Apr. 9, 2020. As the input portion of this particular training time series, the model manager 802 may select a 12-hour portion, such as from 1:59:00 PM on Apr. 8, 2020 to 1:59:00 AM on Apr. 9, 2020. It follows then that the expected output portion of this particular training time series spans from 1:59:00 AM on Apr. 9, 2020 to 2:04:00 AM on Apr. 9, 2020. In scenarios in which the machine learning model 406 is not configured to generate the predicted upcoming glucose measurements 408 in a stepwise manner—but rather in a single pass through the model—the model manager 802 may use, for the expected output portion, a portion of the training time series that corresponds to an entire amount of time of the predicted upcoming glucose measurements 408, e.g., 30 minutes following the input portion. Accordingly, once built, the machine learning model 406 is configured to predict traces of glucose measurements that correspond in amount of time to the expected output portions of the training time series.

The model manager 802 uses the training input portions along with the respective expected output portions to train the machine learning model 406. In the context of training, the model manager 802 may train the machine learning model 406 by providing an instance of data from the set of training input portions to the machine learning model 406. Responsive to this, the machine learning model 406 generates a prediction of upcoming glucose measurements, such as by predicting a timestep of upcoming glucose measurements in stepped implementations (e.g., LSTM) or predicting an entire interval in non-stepped implementations (e.g., other types of neural networks). The model manager 802 obtains this training prediction from the machine learning model 406 as output and compares the training prediction to the expected output portion that corresponds to the training input portion. Based on this comparison, the model manager adjusts internal weights of the machine learning model 406 so that the machine learning model can substantially reproduce the expected output portion when the respective training input portion is provided as input in the future.

This process of inputting instances of the training input portions into the machine learning model 406, receiving training predictions from the machine learning model 406, comparing the training predictions to the expected output portions (observed) that correspond to the input instances (e.g., using a loss function such as mean squared error), and adjusting internal weights of the machine learning model 406 based on these comparisons, can be repeated for hundreds, thousands, or even millions of iterations—using an instance of training data per iteration.

The model manager 802 may perform such iterations until the machine learning model 406 is able to generate predictions that consistently and substantially match the expected output portions. The capability of a machine learning model to consistently generate predictions that substantially match expected output portions may be referred to as "convergence." Given this, it may be said that the model manger 802 trains the machine learning model 406 until it "converges" on a solution, e.g., the internal weights of the model have been suitably adjusted due to training iterations so that the model consistently generates predictions that substantially match the expected output portions.

As noted above, the machine learning model 406 may be configured to receive input in addition to an interval (e.g., an input window) of time series glucose measurements in one or more implementations. In such implementations, the model manager 802 may form training instances that include the training input portion, the respective expected output portion and also additional input data describing any other aspects of the user population 110 being used to predict upcoming glucose measurements, e.g., insulin administrations, carbohydrate consumption, exercise, and/or stress. This additional data as well as the training input portion may be processed by the model manger 802 according to one or more known techniques to produce an input vector. This input vector, describing the training input portion as well as the other aspects, may then be provided to the machine learning model 406. In response, the machine learning model 406 may generate a prediction of upcoming glucose measurements in a similar manner as discussed above, such that the prediction can be compared to the expected output portion of the training instance and weights of the model adjusted based on the comparison.

As also noted above, management of the machine learning model 406 may include personalizing the machine learning model 406 using transfer learning. In such scenarios, the model manager 802 may initially train the machine learning model 406 at the global level, as described in detail above using instances of training data generated from the data of the user population 110. In transfer learning scenarios, the model manager 802 may then create an instance of this globally trained model for a particular user, such that a copy of the globally trained model is generated for the person 102 and other copies of the globally trained model are generated for other users on a per-user basis.

This globally trained model may then be updated (or further trained) using data specific to the person 102. For example, the model manager 802 may create instances of training data using the glucose measurements 118 of the person 102, and further train the globally trained version of model in a similar manner as described above, e.g., by providing training input portions of the person 102's training data to the machine learning model 406, receiving training predictions of upcoming glucose measurements, comparing those predictions to respective output portions of the training data, and adjusting internal weights of the machine learning model 406. Based on this further training, the machine learning model 406 is trained at a personal level, creating a personally trained machine learning model 406.

It is to be appreciated that the personalizing may be less granular than on a per-user basis, in one or more implementations. For example, the globally trained model may be personalized at a user segment level, i.e., a set of similar users of the user population 110 that is less than an entirety of the user population 110. In this way, the model manager 802 may create copies of the globally trained machine learning model 406 on a per-segment basis and train the global versions at the segment level, creating segment specific machine learning models 406.

In one or more implementations, the model manager 802 may personalize the machine learning model 406 at the server level, e.g., at servers of the glucose monitoring platform 112. This model may then be maintained at the server level and/or communicated to the computing device 108, e.g., for integration with an application of the glucose monitoring platform 112 at the computing device 108. Alternately or additionally, at least a portion of the model manager 802 may be implemented at the computing device 108, such that the globally trained version of the machine learning model 406 is communicated to the computing device 108 and the transfer learning (i.e., the further training discussed above to personalize the model) is carried out at the computing device 108. Although transfer learning may be leveraged in one or more scenarios, it is to be appreciated that in other scenarios such personalization may not be utilized and the described techniques may be implemented using globally trained versions of the machine learning model 406.

As also noted above, the machine learning model 406 may be configured as an LSTM network in one or more implementations. With reference to FIG. 5, each of the steps of the machine learning model 406(1)-(5) may correspond to a cell of the LSTM network. In this context, the model manger 802 during training may adjust weights of the different layers of the LSTM network, including weights of a sigmoid layer referred to as the "forget gate layer," weights of a second sigmoid layer referred to as the "input gate layer," weights of a tanh layer that creates a vector of candidate values, and weights of a third sigmoid layer referred to as the "output layer." To adjust these weights, the model manager 802 may back-propagate error values from the output layers, such that the error remains in the LSTM's cell. By doing so, the model manager 802 continuously feeds error back to each of the LSTM cell's layers, until the layers learn to cut off the value during training.

Figure 9:
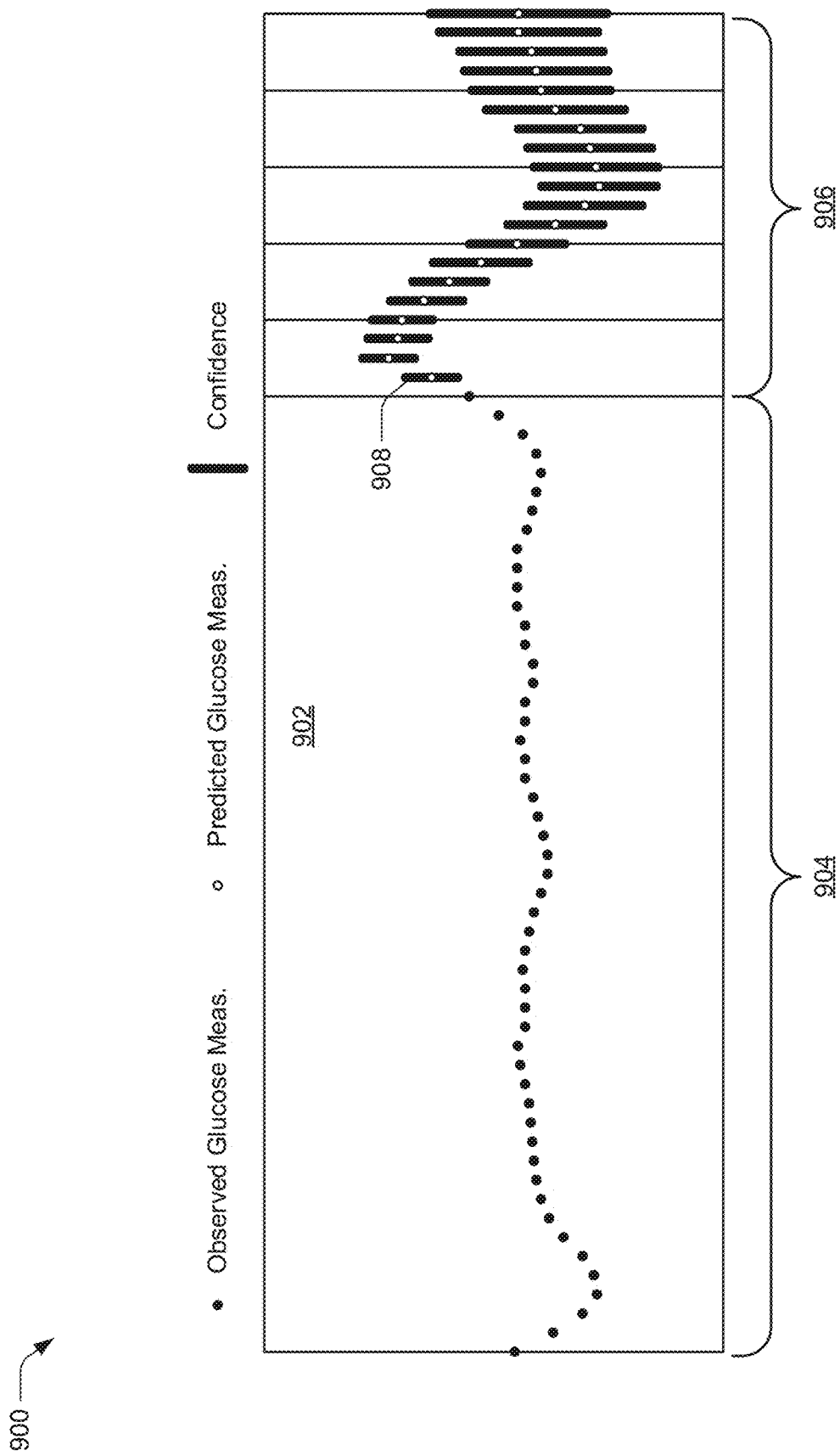
FIG. 9 depicts an example visualization of glucose traces with predicted glucose measurements and confidences in the predictions.

FIG. 9 depicts an example visualization 900 of glucose traces with predicted glucose measurements and confidences in the predictions.

The illustrated example 900 depicts a glucose trace 902 having observed glucose measurements 904 and predicted glucose measurements 906, e.g., the combination forming an "augmented" glucose trace. Additionally, the illustrated example includes visualizations of confidence 908. In particular, each visualization of confidence 908 represents a confidence of the respective predicted glucose measurement 906, e.g., a confidence that the prediction is correct. In this example 900, the visualizations of confidence 908 become larger in size the further away (in terms of time) the predicted glucose measurements 906 are from the observed glucose measurements 904. This reflects that the further in time the predicted glucose measurements 906 are from the observed glucose measurements 904, the less confident the machine learning model 406 is in those predictions. The visualizations of confidence 908 may represent, for instance, a range of glucose within which the machine learning model 406 is 70% confident an observed glucose measurement will be produced at the respective time.

In one or more implementations, the machine learning model 406 may output one or more measures of confidence along with the stepwise glucose traces 502-510 and/or the predicted upcoming glucose measurements 408. In connection with implementations in which the machine learning model 406 outputs measures of confidence with the stepwise glucose traces, the machine learning model 406 may also be configured to receive those measures as input at each step. The machine learning model 406 may use the input measures of confidence to compute the measures of confidence for the next step. In addition or alternately, the machine learning model 406 may be configured to generate a glucose trace at a next step as long the measures of confidence satisfy a threshold. If the glucose trace generated at a previous step is associated with confidence measures that fail to satisfy the threshold, however, then the machine learning model 406 may not generate any further glucose traces.

By using confidence measures in this way, a length of the predicted upcoming glucose measurements 408 may be based on a confidence in the stepwise predictions and not a predetermined interval of time. Nonetheless, one or more implementations may generate glucose traces in the above-discussed stepwise manner for a fixed interval of time.

As discussed above in relation to FIG. 3, the data analytics platform 122 may generate and deliver notifications 314 based on a prediction 312, such as based on the predicted upcoming glucose measurements 408. As noted above, the machine learning model 406 is capable of predicting glucose accurately for further predictive horizons from a current time than conventional techniques. These more accurate predictions of glucose can in turn be used to predict whether a patient will experience an upcoming glycemic event, such as overnight hypoglycemia. To this end, the glucose predictions generated by the machine learning model 406 may serve as input to one or more decision support models, which can alert or otherwise inform users about upcoming glycemic events. For instance, the data analytics platform 122 may deliver an alert or support for deciding how to treat diabetes. In this context, consider FIG. 10 which depicts example notifications.

Figure 10:
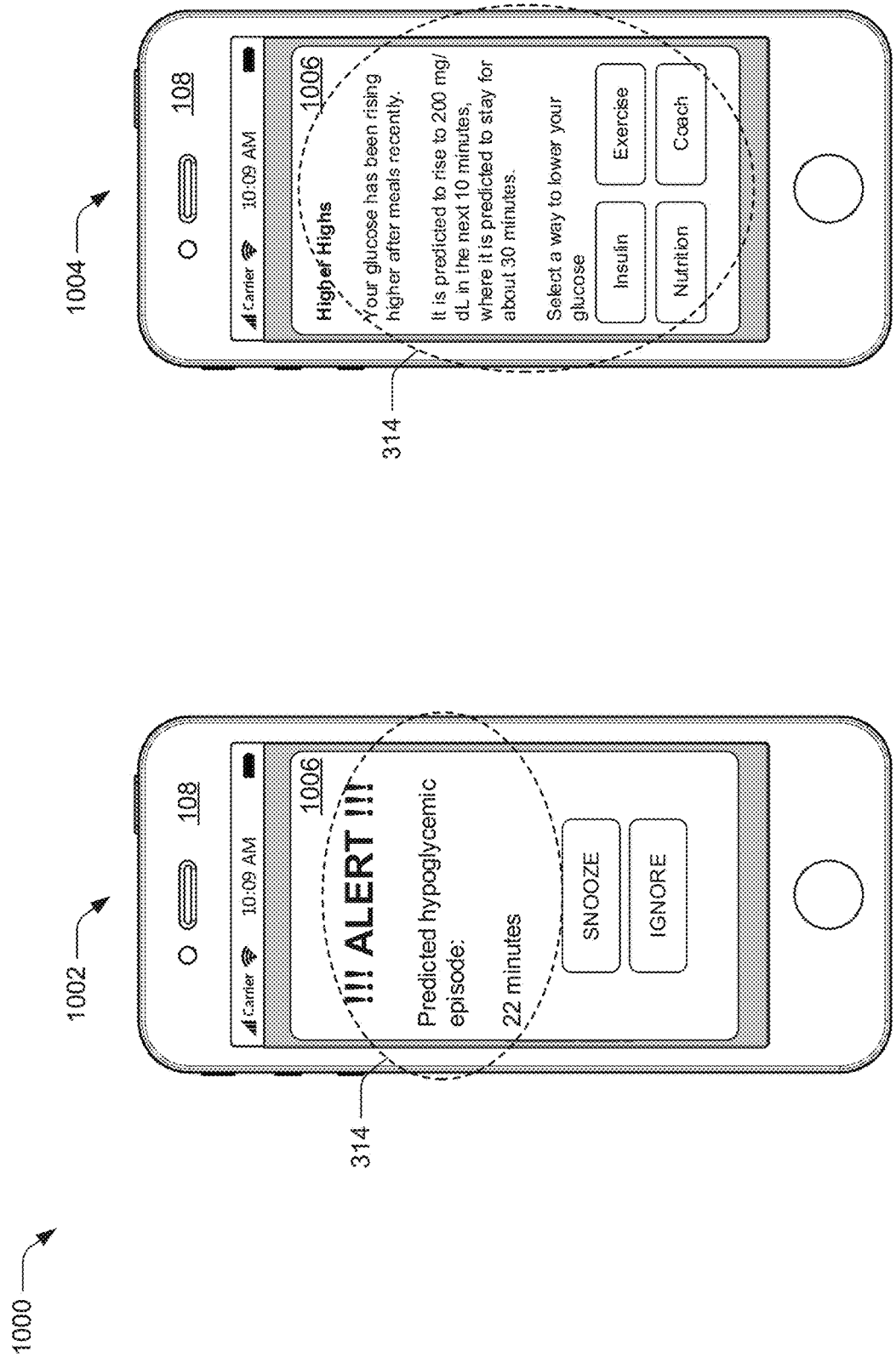
FIG. 10 depicts example implementations of user interfaces displayed for notifying a user based on a prediction of upcoming glucose measurements.

FIG. 10 depicts example implementations 1000 of user interfaces displayed for notifying a user based on predictions of upcoming glucose measurements. In particular, the example implementations 1000 include the computing device 108 depicted in an alert scenario 1002 and a decision support scenario 1004.

In both the alert and decision support scenarios 1002, 1004, the computing device 108 displays a user interface 1006. The user interface 1006 may correspond to an interface of an application, e.g., an interface of an application of the glucose monitoring platform 112. Alternately or additionally, the user interface 1006 may correspond to a notification "center", such as a lock screen or other operating-level screen.

In the alert scenario 1002, the user interface 1006 displays an alert notification 314 via a display device of the computing device 108. This notification 314 may be configured to alert a user about an upcoming adverse health condition, such as that the user is likely to experience dysglycemia (i.e., hyper- or hypo-glycemia) absent a mitigating behavior (e.g., eating, taking insulin, exercise, and so forth). In accordance with the described techniques, this notification 314 is based on the predicted upcoming glucose measurements 408, which in this example may be processed to identify a predicted hypoglycemic episode in 22 minutes. It is to be appreciated that notifications may cause computing device to output different signals in addition to displaying information, including, for instance, audio signals via speakers, vibrations or other haptics via haptic systems, and so forth.

In the decision support scenario 1004, the user interface 1006 displays a support notification 314 via the display device of the computing device 108. This notification 314 may be configured to provide support for deciding how to treat diabetes, such as by recommending a user perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on. In accordance with the described techniques, this notification 314 is also based on the predicted upcoming glucose measurements 408.

Although notifications to a user are shown, it is to be appreciated that in one or more implementations, notifications generated based on the predicted upcoming glucose measurements 408 may alternately or additionally be communicated to other entities, such as a health care provider of the person 102 (e.g., a doctor), a caregiver of the person 102 (e.g., a parent or a child), a telemedicine service, and so forth. Further, it is to be appreciated that a variety of other services in addition or alternate to notification services may be provided based on the predicted upcoming glucose measurements 408 without departing from the spirit or scope of the described techniques.

Having discussed example details of the techniques for glucose prediction using machine learning and time series glucose measurements, consider now some example procedures to illustrate additional aspects of the techniques.

Example Procedures

This section describes example procedures for glucose prediction using machine learning and time series glucose measurements. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by a prediction system, such as the prediction system 310 that makes use of the sequencing manager 404, the machine learning model 406, and the model manager 802.

Figure 11:
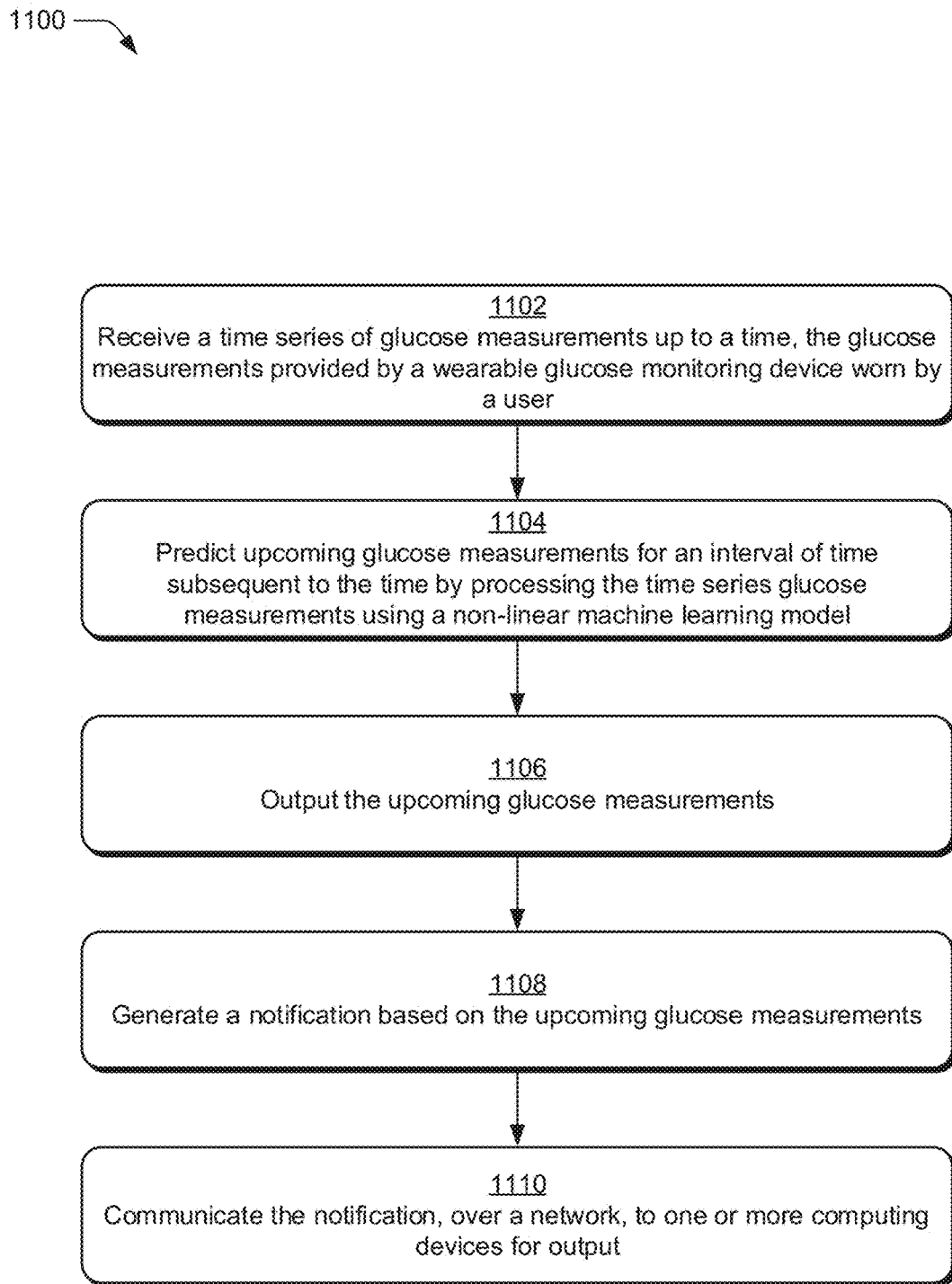
FIG. 11 depicts a procedure in an example implementation in which a non-linear machine learning model predicts upcoming glucose measurements based on time series glucose measurements.

FIG. 11 depicts a procedure 1100 in an example implementation in which a non-linear machine learning model predicts upcoming glucose measurements based on time series glucose measurements.

A time series of glucose measurements up to a time is received (block 1102). In accordance with the principles discussed herein, the glucose measurements are provided by a wearable glucose monitoring device worn by a user. By way of example, the machine learning model 406 receives the time series glucose measurements 410, and the glucose measurements are provided by the wearable glucose monitoring device 104 worn by the person 102. In particular, the wearable glucose monitoring device 104 includes the sensor 202, which is inserted subcutaneously into skin of the person 102 and used to measure glucose in the person 102's blood. As discussed above, the wearable glucose monitoring device 104 may be configured as a continuous glucose monitoring (CGM) system.

Upcoming glucose measurements are predicted for an interval of time subsequent to the time (block 1104). In accordance with the principles discussed herein, the upcoming glucose measurements are predicted by processing the time series glucose measurements using a non-linear machine learning model generated based on historical time series of glucose measurements of a user population. By way of example, the machine learning model 406 generates the predicted upcoming glucose measurements 408. The machine learning model 406 generates this prediction by processing the time series glucose measurements 410 based on patterns, learned during training, of time series of the glucose measurements 118 of the user population 110. As noted above, the user population 110 includes users that wear wearable glucose monitoring device, such as the wearable glucose monitoring device 104.

The upcoming glucose measurements are output (block 1106). By way of example, the prediction system 310 outputs the predicted upcoming glucose measurements 408, such as for processing by additional logic (e.g., to generate recommendations or notifications), for storing in the storage device 120, for communication to one or more computing devices, or for display, to name just a few.

A notification is generated based on the upcoming glucose measurements (block 1108). By way of example, the data analytics platform 122 generates the notification 314 based on the predicted upcoming glucose measurements 408. For instance, the notification 314 may alert a user (or a health care provider or telemedicine service) about an upcoming adverse health condition, such as that the user is likely to experience dysglycemia (i.e., hyper- or hypoglycemia) absent a mitigating behavior (e.g., eating, taking insulin, exercise, and so forth). In addition or alternately, the notification 314 may provide support for deciding how to treat diabetes, such as by recommending a user (or a health care provider or telemedicine service) perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on.

The notification is communicated, over a network, to one or more computing device for output (block 1110). By way of example, a communication interface of the data analytics platform 122 communicates the notification 314 over the network 116 to the computing device 108 of the person 102, e.g., for output via an application of the glucose monitoring platform 112. Alternately or in addition, the data analytics platform 122 communicates the notification 314 over the network 116 to a computing device associated with a health care provider (not shown) and/or a computing device associated with a telemedicine service (not shown), e.g., for output via a provider portal.

Figure 12:
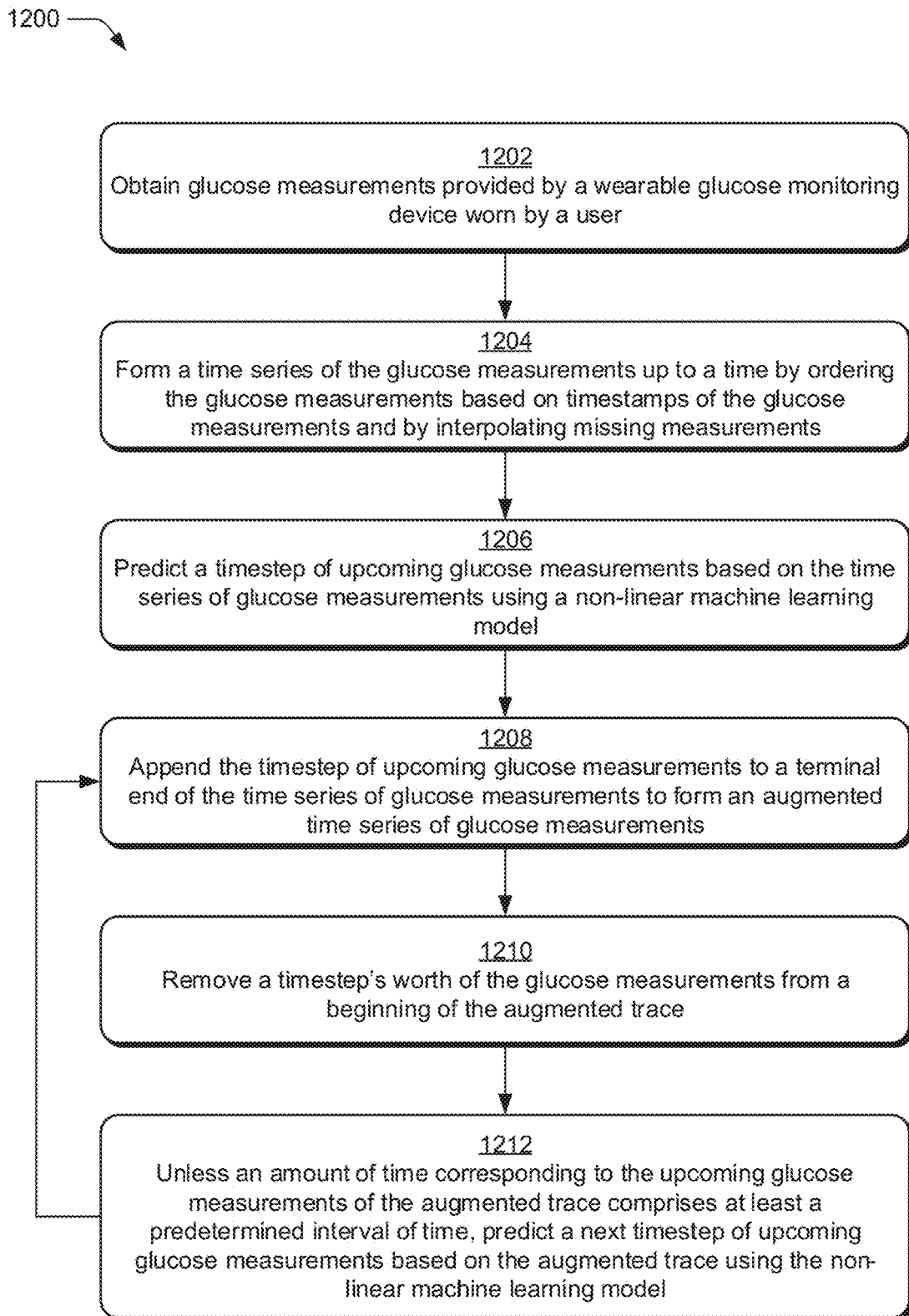
FIG. 12 depicts a procedure in an example implementation in which a non-linear machine learning model iteratively predicts upcoming glucose measurements until an interval of time of the measurements is predicted.

FIG. 12 depicts a procedure 1200 in an example implementation in which a non-linear machine learning model iteratively predicts upcoming glucose measurements until an interval of time of the measurements is predicted.

Glucose measurements are obtained that have been provided by a wearable glucose monitoring device worn by a user (block 1202). By way of example, the sequencing manager 404 obtains the glucose measurements 118 of the person 102 and the timestamps 402 of those measurements.

A time series of the glucose measurements up to a time is formed (block 1204). In accordance with the principles discussed herein, the time series of glucose measurements is formed by ordering the glucose measurements according to respective timestamps and by interpolating missing measurements. By way of example, the sequencing manager 404 forms the time series glucose measurements 410 (e.g., up to a measurement last received from the wearable glucose monitoring device 104) by ordering the glucose measurements 118 according to the timestamps 402. The sequencing manager 404 also interpolates missing measurements, such as measurements missing due to data corruption or communication errors.

A timestep of upcoming glucose measurements is predicted based on the time series of glucose measurements using a non-linear machine learning model (block 1206). By way of example, the machine learning model 406(1) generates the first timestep of glucose measurements 606 based on the time series glucose measurements 410.

The timestep of upcoming glucose measurements is appended to a terminal end of the time series of glucose measurements to form an augmented time series of glucose measurements (block 1208). By way of example, the machine learning model 406(1) (or additional logic) appends the first timestep of glucose measurements 606 to a terminal end of the time series glucose measurements 410 to form the first glucose trace 502, an augmented trace of glucose measurements.

Optionally, a timestep's worth of the glucose measurements are removed from a beginning of the augmented trace (block 1210). By way of example, the machine learning model 406(1) (or the additional logic) removes measurements corresponding to the crossed-out points 604 from the first glucose trace 502.

Unless an amount of time corresponding to the upcoming glucose measurements of the augmented trace comprises at least a predetermined interval time, a next timestep of upcoming glucose measurements is predicted based on the augmented trace using the non-linear machine learning model (block 1212). By way of example, the machine learning model 406(2) generates the second timestep of glucose measurements 608 based on the first glucose trace 502.

The blocks 1208-1212 are repeated until the timesteps of upcoming glucose measurements of the augmented trace in combination span at least the predetermined interval of time. By way of example, the subsequent steps of the machine learning model 406 repeat the steps of blocks 1208-1212 until the timesteps in combination span at least the predetermined interval of time, e.g., six 5-minute timesteps combined span a predetermined 30-minute time interval.

Figure 13:
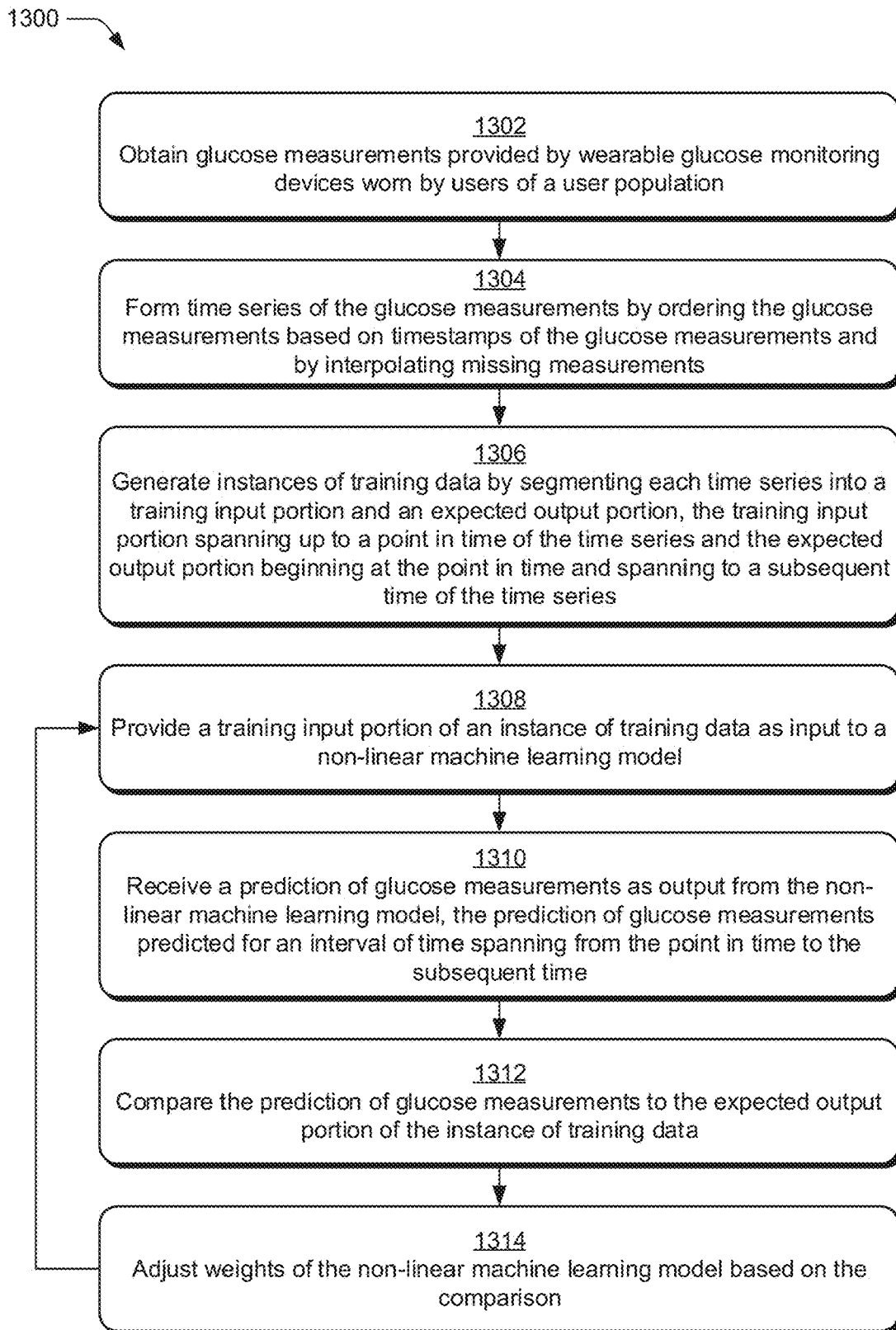
FIG. 13 depicts a procedure in an example implementation in which a non-linear machine learning model is trained to predict upcoming glucose measurements based on historical time series glucose measurements of a user population.

FIG. 13 depicts a procedure 1300 in an example implementation in which a non-linear machine learning model is trained to predict upcoming glucose measurements based on historical time series glucose measurements of a user population.

Glucose measurements provided by wearable glucose monitoring devices worn by users of a user population are obtained (block 1302). By way of example, the sequencing manager 404 obtains the glucose measurements 118 of users of the user population 110 and the timestamps 402 of those measurements.

Time series of the glucose measurements are formed (block 1304). In accordance with the principles discussed herein, the time series of glucose measurements are formed by ordering the glucose measurements according to respective timestamps and by interpolating missing measurements. By way of example, the sequencing manager 404 forms time series of the user population 110's glucose measurements 118 by ordering the user population 110's glucose measurements 118 according to the respective timestamps 402. The sequencing manager 404 also interpolates missing measurements, such as measurements missing due to data corruption or communication errors.

Instances of training data are generated by segmenting each time series into a training input portion and an expected output portion (block 1306). In accordance with the principles discussed herein, the training input portion spans up to a point in time of the time series and the expected output portion begins substantially at the point in time and spans to a subsequent time of the time series. By way of example, the model manager generates instances of training data by segmenting each of the time series formed at block 1304 into a training input portion and an expected output portion.

Here, blocks 1308-1314 may be repeated until a non-linear machine learning model is suitably trained, such as until the non-linear machine learning model "converges" on a solution, e.g., the internal weights of the model have been suitably adjusted due to training iterations so that the model consistently generates predictions that substantially match the expected output portions. Alternately or in addition, the blocks 1308-1314 may be repeated for a number of instances (e.g., all instances) of the training data.

A training input portion of an instance of training data is provided as input to the non-linear machine learning model (block 1308). By way of example, the model manager 802 provides a training input portion of an instance of training data generated at block 1306 as input to the machine learning model 406.

A prediction of glucose measurements is received as output from the non-linear machine learning model (block 1310). In accordance with the principles discussed herein, the prediction of glucose measurements is predicted for an interval of time spanning substantially from the point in time to the subsequent time. By way of example, the machine learning model 406 predicts a timestep of upcoming glucose measurements based on the training input portion provided at block 1308, and the model manager 802 receives the timestep of upcoming glucose measurements as output of the machine learning model 406.

The prediction of glucose measurements is compared to the expected output portion of the instance of training data (block 1312). By way of example, the model manager compares the timestep of upcoming glucose measurements predicted at block 1310 to the expected output portion of the training instance generated at block 1306, e.g., by using a loss function such as mean squared error (MSE). It is to be appreciated that the model manager 802 may use other loss functions during training, to compare the predictions of the machine learning model 406 to the expected output, without departing from the spirit or scope of the described techniques.

Weights of the non-linear machine learning model are adjusted based on the comparison (block 1314). By way of example, the model manager 802 may adjust internal weights of the machine learning model 406 based on the comparing. In one or more implementations, the model manager 802 may optionally leverage one or more hyperparameter optimization techniques (e.g., a Bayesian-optimized grid search) during training to tune hyperparameters of the learning algorithm employed.

Having described example procedures in accordance with one or more implementations, consider now an example system and device that can be utilized to implement the various techniques described herein.

Example System and Device

Figure 14:
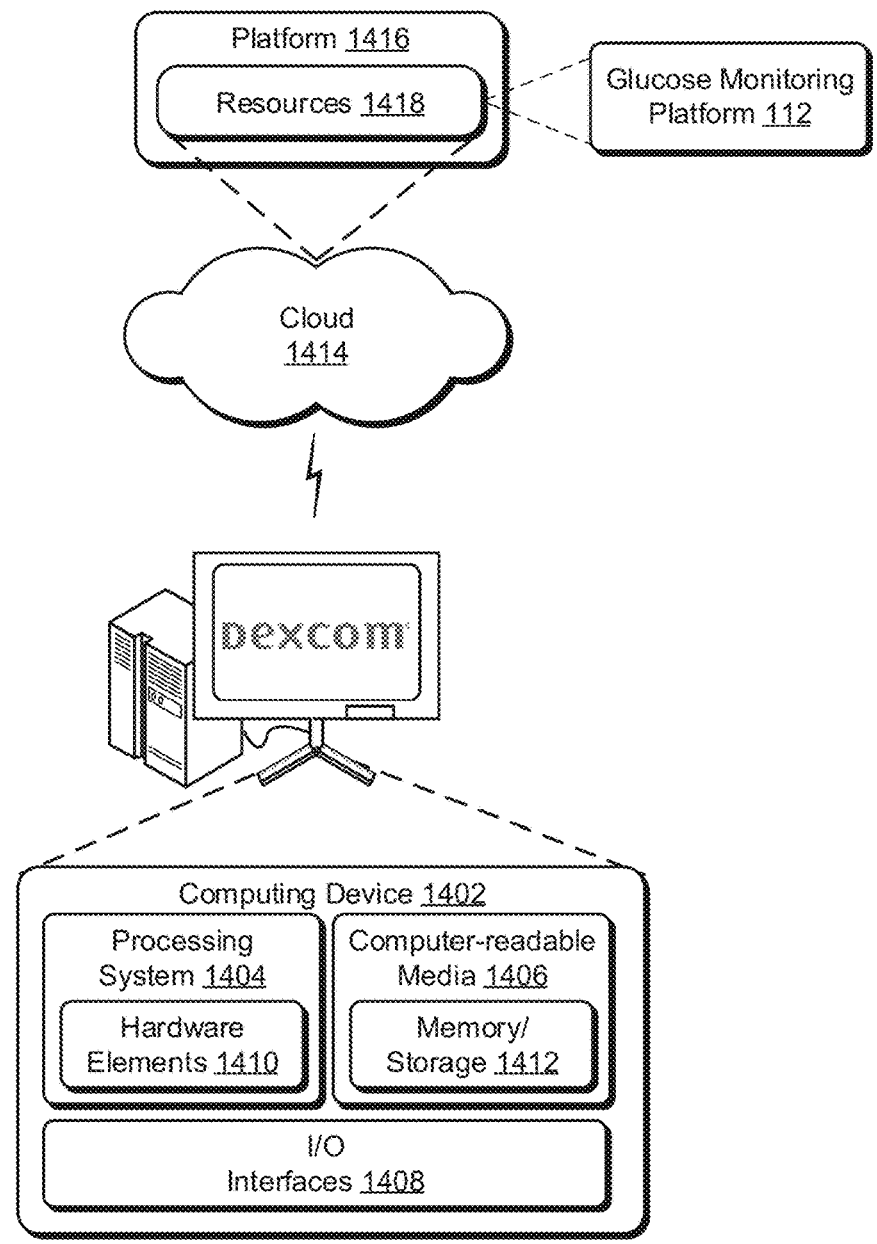
FIG. 14 illustrates an example system including various components of an example device that can be implemented as any type of computing device as described and/or utilized with reference to FIGS. 1-13 to implement embodiments of the techniques described herein.

FIG. 14 illustrates an example system generally at 1400 that includes an example computing device 1402 that is representative of one or more computing systems and/or devices that may implement the various techniques described herein. This is illustrated through inclusion of the glucose monitoring platform 112. The computing device 1402 may be, for example, a server of a service provider, a device associated with a client (e.g., a client device), an on-chip system, and/or any other suitable computing device or computing system.

The example computing device 1402 as illustrated includes a processing system 1404, one or more computer-readable media 1406, and one or more I/O interfaces 1408 that are communicatively coupled, one to another. Although not shown, the computing device 1402 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1404 is representative of functionality to perform one or more operations using hardware. Accordingly, the processing system 1404 is illustrated as including hardware elements 1410 that may be configured as processors, functional blocks, and so forth. This may include implementation in hardware as an application specific integrated circuit or other logic device formed using one or more semiconductors. The hardware elements 1410 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 1406 is illustrated as including memory/storage 1412. The memory/storage 1412 represents memory/storage capacity associated with one or more computer-readable media. The memory/storage component 1412 may include volatile media (such as random access memory (RAM)) and/or nonvolatile media (such as read only memory (ROM), Flash memory, optical disks, magnetic disks, and so forth). The memory/storage component 1412 may include fixed media (e.g., RAM, ROM, a fixed hard drive, and so on) as well as removable media (e.g., Flash memory, a removable hard drive, an optical disc, and so forth). The computer-readable media 1406 may be configured in a variety of other ways as further described below.

Input/output interface(s) 1408 are representative of functionality to allow a user to enter commands and information to computing device 1402, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1402 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1402. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1402, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1410 and computer-readable media 1406 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1410. The computing device 1402 may be configured to implement particular instructions and/or functions corresponding to the software and/or hardware modules. Accordingly, implementation of a module that is executable by the computing device 1402 as software may be achieved at least partially in hardware, e.g., through use of computer-readable storage media and/or hardware elements 1410 of the processing system 1404. The instructions and/or functions may be executable/operable by one or more articles of manufacture (for example, one or more computing devices 1402 and/or processing systems 1404) to implement techniques, modules, and examples described herein.

The techniques described herein may be supported by various configurations of the computing device 1402 and are not limited to the specific examples of the techniques described herein. This functionality may also be implemented all or in part through use of a distributed system, such as over a "cloud" 1414 via a platform 1416 as described below.

The cloud 1414 includes and/or is representative of a platform 1416 for resources 1418. The platform 1416 abstracts underlying functionality of hardware (e.g., servers) and software resources of the cloud 1414. The resources 1418 may include applications and/or data that can be utilized while computer processing is executed on servers that are remote from the computing device 1402. Resources 1418 can also include services provided over the Internet and/or through a subscriber network, such as a cellular or Wi-Fi network.

The platform 1416 may abstract resources and functions to connect the computing device 1402 with other computing devices. The platform 1416 may also serve to abstract scaling of resources to provide a corresponding level of scale to encountered demand for the resources 1418 that are implemented via the platform 1416. Accordingly, in an interconnected device embodiment, implementation of functionality described herein may be distributed throughout the system 1400. For example, the functionality may be implemented in part on the computing device 1402 as well as via the platform 1416 that abstracts the functionality of the cloud 1414.

Conclusion

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method comprising:
receiving a time series of glucose measurements up to a time, the glucose measurements provided by a wearable glucose monitoring device worn by a patient;
receiving a patient-specific correction factor determined for the patient based on historical glucose measurements for the patient and device data of the wearable glucose monitoring device worn by the patient;
generating, using a machine learning model:
a first set of predicted upcoming glucose measurements for the patient over an interval of time subsequent to the time; and
a first set of confidence measures for the first set of predicted upcoming glucose measurements, wherein:
the first set of predicted upcoming glucose measurements and the first set of confidence measures are based upon the time series of glucose measurements and the patient-specific correction factor, and
the machine learning model is trained using historical time series of glucose measurements of a patient population;
outputting the first set of predicted upcoming glucose measurements and the first set of confidence measures on a display of a user device;
generating, using the machine learning model:
a second set of predicted upcoming glucose measurements for the patient; and
a second set of confidence measures for the second set of predicted upcoming glucose measurements, wherein:
the second set of predicted upcoming glucose measurements and the second set of confidence measures are based upon the time series of glucose measurements, the first set of predicted upcoming glucose measurements, and the first set of confidence measures; and
outputting the second set of predicted upcoming glucose measurements and the second set of confidence measures on the display.

2. The method as described in claim 1, further comprising generating a notification based on the first set of predicted upcoming glucose measurements and the second set of predicted upcoming glucose measurements, and communicating the notification, over a network, to one or more computing devices for output.

3. The method as described in claim 1, wherein the patient-specific correction factor determined for the patient is further based on:
device data of other glucose monitoring devices previously worn by the patient;
interaction data describing interactions of the patient with the wearable glucose monitoring device;
interaction data describing interactions of the patient with an application of a glucose monitoring platform; and
a status of the patient's wearable glucose monitoring device.

4. The method as described in claim 3, wherein the device data of the wearable glucose monitoring device includes a status of a sensor of the wearable glucose monitoring device.

5. The method as described in claim 2, wherein the notification is an alert about an upcoming adverse health condition.

6. The method as described in claim 1, further comprising sequencing the glucose measurements provided by the wearable glucose monitoring device based on timestamps of the glucose measurements to form the time series of glucose measurements.

7. The method as described in claim 6, further comprising interpolating missing glucose measurements based on the glucose measurements and the timestamps.

8. The method as described in claim 1, wherein the historical time series of glucose measurements comprise measurements provided by wearable glucose monitoring devices worn by patients of the patient population.

9. A system comprising:
one or more processors; and
memory having stored thereon computer-readable instructions that are executable by the one or more processors to perform operations comprising:
receiving a time series of glucose measurements up to a time, the glucose measurements provided by a wearable glucose monitoring device worn by a patient;
receiving a patient-specific correction factor determined for the patient based on historical glucose measurements for the patient and device data of the wearable glucose monitoring device worn by the patient;
generating, using a machine learning model:
a first set of predicted upcoming glucose measurements for the patient over an interval of time subsequent to the time; and
a first set of confidence measures for the first set of predicted upcoming glucose measurements, wherein:
the first set of predicted upcoming glucose measurements and the first set of confidence measures are based upon the time series of glucose measurements and the patient-specific correction factor, and
the machine learning model is trained using historical time series of glucose measurements of a patient population;
outputting the first set of predicted upcoming glucose measurements and the first set of confidence measures on a display of a user device;

generating, using the machine learning model:
a second set of predicted upcoming glucose measurements for the patient; and
a second set of confidence measures for the second set of predicted upcoming glucose measurements, wherein:
the second set of predicted upcoming glucose measurements and the second set of confidence measures are based upon the time series of glucose measurements, the first set of predicted upcoming glucose measurements, and the first set of confidence measures; and
outputting the second set of predicted upcoming glucose measurements and the second set of confidence measures on the display.

10. The system as described in claim 9, wherein the operations further comprise generating a notification based on the first set of predicted upcoming glucose measurements and the second set of predicted upcoming glucose measurements, and communicating the notification, over a network, to one or more computing devices for output.

11. The system as described in claim 9, wherein the patient-specific correction factor is determined for the patient is further based on:
device data of other glucose monitoring devices previously worn by the patient;
interaction data describing interactions of the patient with the wearable glucose monitoring device;
interaction data describing interactions of the patient with an application of a glucose monitoring platform; and
a status of the patient's wearable glucose monitoring device.

12. The system as described in claim 9, wherein the device data of the wearable glucose monitoring device includes a status of a sensor of the wearable glucose monitoring device.

13. The system as described in claim 9, wherein the machine learning model is a neural network that iteratively predicts additional upcoming glucose measurements.

14. The system as described in claim 9, wherein the machine learning model is a long-short term memory (LSTM) network that iteratively predicts additional upcoming glucose measurements.

15. The system as described in claim 9, wherein the operations further comprise sequencing the glucose measurements provided by the wearable glucose monitoring device based on timestamps of the glucose measurements to form the time series of glucose measurements.

16. The system as described in claim 15, wherein the operations further comprise interpolating missing glucose measurements based on the glucose measurements and the timestamps.

17. One or more computer-readable storage media having instructions stored thereon that are executable by one or more processors to perform operations comprising:

receiving a time series of glucose measurements up to a time, the glucose measurements provided by a wearable glucose monitoring device worn by a patient;
receiving a patient-specific correction factor determined for the patient based on historical glucose measurements for the patient and device data of the wearable glucose monitoring device worn by the patient;
generating, using a machine learning model:
a first set of predicted upcoming glucose measurements for the patient over an interval of time subsequent to the time; and
a first set of confidence measures for the first set of predicted upcoming glucose measurements, wherein:
the first set of predicted upcoming glucose measurements and the first set of confidence measures are based upon the time series of glucose measurements and the patient-specific correction factor, and
the machine learning model is trained using historical time series of glucose measurements of a patient population;
outputting the first set of predicted upcoming glucose measurements and the first set of confidence measures on a display of a user device;
generating, using the machine learning model:
a second set of predicted upcoming glucose measurements for the patient; and
a second set of confidence measures for the second set of predicted upcoming glucose measurements, wherein:
the second set of predicted upcoming glucose measurements and the second set of confidence measures are based upon the time series of glucose measurements, the first set of predicted upcoming glucose measurements, and the first set of confidence measures; and
outputting the second set of predicted upcoming glucose measurements and the second set of confidence measures on the display.

18. The method as described in claim 1, wherein the first set of predicted upcoming glucose measurements, the first set of confidence measures, the second set of predicted upcoming glucose measurements, and the second set of confidence measures are output at the same time.

19. The system as described in claim 9, wherein the first set of predicted upcoming glucose measurements, the first set of confidence measures, the second set of predicted upcoming glucose measurements, and the second set of confidence measures are output at the same time.

20. The one or more computer readable storage media as described in claim 17, wherein the first set of predicted upcoming glucose measurements, the first set of confidence measures, the second set of predicted upcoming glucose measurements, and the second set of confidence measures are output at the same time.

* * * * *